(12) United States Patent
Herzog et al.

(10) Patent No.: US 9,283,160 B2
(45) Date of Patent: Mar. 15, 2016

(54) STABILIZATION OF COSMETIC COMPOSITIONS

(75) Inventors: Bernd Herzog, Grenzach-Wyhlen (DE); Julie Grumelard, Huningue (FR)

(73) Assignee: BASF SE, Ludwigshafen (DE)

( * ) Notice: Subject to any disclaimer, the term of this patent is extended or adjusted under 35 U.S.C. 154(b) by 259 days.

(21) Appl. No.: 13/144,113

(22) PCT Filed: Jan. 28, 2010

(86) PCT No.: PCT/EP2010/051011
§ 371 (c)(1),
(2), (4) Date: Aug. 11, 2011

(87) PCT Pub. No.: WO2010/091963
PCT Pub. Date: Aug. 19, 2010

(65) Prior Publication Data
US 2011/0305650 A1    Dec. 15, 2011

(30) Foreign Application Priority Data

Jan. 29, 2009   (EP) .................................... 09151614

(51) Int. Cl.
| | | |
|---|---|---|
| *A61Q 17/04* | (2006.01) | |
| *A61K 8/36* | (2006.01) | |
| *A61K 8/37* | (2006.01) | |
| *A61K 8/40* | (2006.01) | |
| *A61K 8/41* | (2006.01) | |
| *A61K 8/49* | (2006.01) | |

(52) U.S. Cl.
CPC ... *A61K 8/36* (2013.01); *A61K 8/37* (2013.01); *A61K 8/40* (2013.01); *A61K 8/411* (2013.01); *A61K 8/496* (2013.01); *A61K 8/4966* (2013.01); *A61Q 17/04* (2013.01); *A61K 2800/52* (2013.01)

(58) Field of Classification Search
USPC ........................................................ 424/59
See application file for complete search history.

(56) References Cited

U.S. PATENT DOCUMENTS

| | | | |
|---|---|---|---|
| 6,015,548 A * | 1/2000 | Siddiqui et al. ................. | 424/59 |
| 2002/0001570 A1 | 1/2002 | Heidenfelder et al. | |
| 2005/0008587 A1 | 1/2005 | Schulz et al. | |
| 2009/0035238 A1 | 2/2009 | Pfluecker et al. | |

FOREIGN PATENT DOCUMENTS

| | | |
|---|---|---|
| DE | 100 12 408 A1 | 9/2001 |
| DE | 101 55 963 A1 | 5/2003 |
| DE | 10 2006 006413 A1 | 8/2007 |
| DE | 10 2007 005334 A1 | 8/2008 |
| EP | 1352639 A | 10/2003 |
| WO | 2006034968 A | 4/2006 |
| WO | 2007/071584 A | 6/2007 |

OTHER PUBLICATIONS

Gaspar et al, Evaluation of the photostability of different UV filter combinations in a sunscreen, International journal of pharmecautics 307 (2006) 123-128.*
English Language Abstract of WO 2008/092672 (Which Is an = of DE 10 2007 005334) Aug. 2008.
English Language Abstract of EP 1352639 Oct. 2003.
IP.com Journal, "Amino substituted hydroxyphenyl benzophenone derivatives" p. 11, 2003.

* cited by examiner

*Primary Examiner* — Jennifer A Berrios
(74) *Attorney, Agent, or Firm* — Marshall, Gerstein & Borun LLP

(57) ABSTRACT

Disclosed is the Use of UV absorbers selected from ($a_1$) diphenylacrylates; and ($a_2$) specific hydroxyphenyl triazines for stabilizing cosmetic compositions comprising an organic UV absorber selected from ($b_1$) a specific benzophenone derivative, ($b_2$) a specific benzotriazole derivative and ($b_3$) a specific triazine derivative and UV filters selected from ($c_1$) cinnamic acid derivatives; and ($c_2$) dibenzoylmethane derivatives.

2 Claims, No Drawings

STABILIZATION OF COSMETIC COMPOSITIONS

It is well known that ultraviolet radiation (light) is harmful to human skin. Depending on the wavelength the UV radiation causes different types of skin damage. UV-B radiation (about 290 to about 320 nm) is responsible for sunburn and can cause skin cancer. UV-A radiation (about 320 to about 400 nm) while producing tanning of the skin, contributes also to sunburn and the induction of skin cancers. Moreover, the harmful effects of the UV-B radiation may be aggravated by UV-A radiation.

Therefore, an effective sunscreen formulation preferably comprises both at least one UV-A and UV-B filter covering the full range of about 290 nm to about 400 nm to prevent the human skin from the harmful effects of sunlight.

The effects of UV-A are mainly mediated by free radicals, e.g. reactive oxygen species inducing different types of degradation to cellular DNA, lipids, and proteins. The visible indications are often the result of long-term, cumulative effects. This is why skin photoaging is associated with UV-A light. It is also known that normal outdoor UV-A radiation can be effective enough to cause the breakdown of the proteins collagen and elastin leading to a loss of firmness and resilience of the skin. Therefore the UVA protection of a daily skin care is of significant relevance.

Numerous UV-B filters are registered for their use in sunscreen preparations, which are mainly derivatives of the 3-benzylidenecamphor, ethylhexyl salicylates and cinnamic acid esters, such as 2-ethylhexyl p-methoxycinnamate.

A new class of organic UV filters are micronized piperazine bi-bisaminobenzophenones which are commonly used in admixture with cinnamic acid derivatives and/or dibenzoyl methane derivatives.

Unfortunately, this UV filter combination employed in sunscreen compositions suffers from relatively rapid photodegradation with the consequence that the protection from sun damage is lost.

One challenge of this invention is therefore to enhance the stability of these specific UV filter combinations.

Surprisingly, it has been found that the use of diphenylacrylates and specific triazine derivatives will enhance the stability of cosmetic and dermatological formulations comprising the combination of specific micronized triazine derivatives and UV absorbers selected from cinnamic acid derivatives and dibenzoyl methane derivatives.

Therefore, the present invention relates to the use of UV absorbers selected from
($a_1$) diphenylacrylates; and
($a_2$) hydroxyphenyl triazines of formula

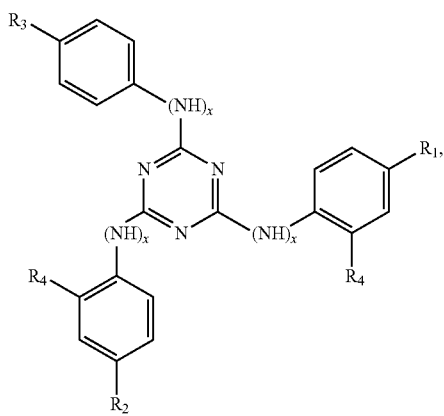

wherein
$R_1$ is —O—$R_5$; —COO$R_6$; or —CO—NH$R_7$;
$R_2$ is —O—$R_8$; —COO$R_9$; or —CO—NH$R_{10}$;
$R_3$ is —O—$R_{11}$; —COO$R_{12}$; or —CO—NH$R_{13}$;
$R_5$, $R_6$, $R_7$, $R_8$, $R_9$, $R_{10}$, $R_{11}$, $R_{12}$ and $R_{13}$ independently from each other are $C_1$-$C_{18}$alkyl;
$R_4$ is hydrogen; or hydroxy; and
x is 0; or 1;
for stabilizing cosmetic compositions comprising an organic UV absorber selected from
($b_1$) a benzophenone derivatives of formula

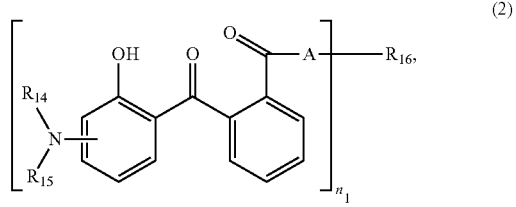

wherein
$R_{14}$ and $R_{15}$ independently from each other are; $C_1$-$C_{20}$alkyl; $C_2$-$C_{20}$alkenyl; $C_3$-$C_{10}$cycloalkyl; $C_3$-$C_{10}$cycloalkenyl; or $R_{14}$ and $R_{15}$ together with the linking nitrogen atom form a 5- or 6-membered heterocyclic ring;
$n_1$ is a number from 1 to 4;
when $n_1$=1,
$R_{16}$ is a saturated or unsaturated heterocyclic radical; hydroxy-$C_1$-$C_5$alkyl; cyclohexyl optionally substituted with one or more $C_1$-$C_5$alkyl; phenyl optionally substituted with a heterocyclic radical, aminocarbonyl or $C_1$-$C_5$alkylcarboxy;
when $n_1$ is 2,
$R_{16}$ is an alkylene-, cycloalkylene alkenylene or phenylene radical which is optionally substituted by a carbonyl- or carboxy group; a radical of formula *—$CH_2$—C≡C—$CH_2$—* or $R_{16}$ together with A forms a bivalent radical of the formula

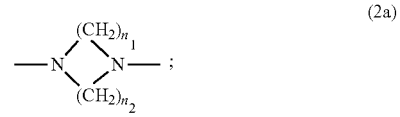

wherein
$n_2$ is a number from 1 to 3;
when $n_1$ is 3,
$R_{16}$ is an alkantriyl radical;
when $n_1$ is 4,
$R_{16}$ is an alkanetetrayl radical;
A is —O—; or —N($R_{17}$)—; and
$R_{17}$ is hydrogen; $C_1$-$C_5$alkyl; or hydroxy-$C_1$-$C_5$alkyl;

($b_2$) a benzotriazole derivative of formula

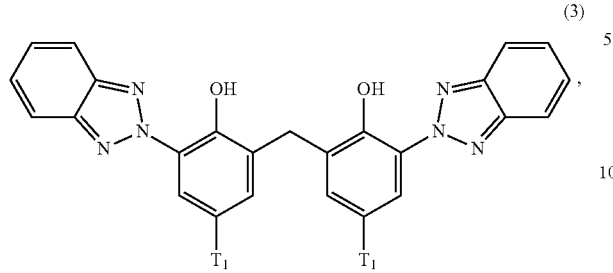

(3)

wherein
$T_1$ is optionally phenyl-substituted $C_1$-$C_{12}$alkyl; and
($b_3$) a triazine derivative of formula

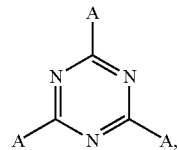

(4)

wherein
A is a radical of formula

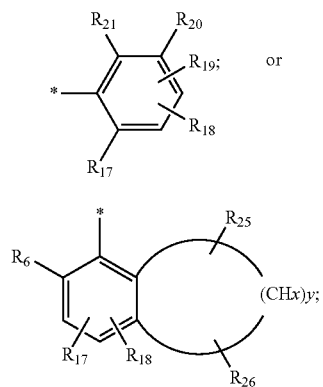

(4a)

(4b)

$R_{17}$ and $R_{21}$ independently from each other are hydrogen; $C_1$-$C_{18}$alkyl; or $C_6$-$C_{12}$aryl;
$R_{18}$, $R_{19}$ and $R_{20}$ independently from each other are hydrogen; or a radical of formula

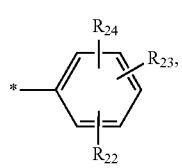

(4c)

wherein, in formula (4a), at least one of the radicals $R_{18}$, $R_{19}$ and $R_{20}$ are a radical of formula (4c);
$R_{22}$, $R_{23}$, $R_{24}$, $R_{25}$ and $R_{26}$ independently from each other are hydrogen; hydroxy; halogen; $C_1$-$C_{18}$alkyl; $C_1$-$C_{18}$alkoxy; $C_6$-$C_{12}$aryl; biphenylyl; $C_6$-$C_{12}$aryloxy; $C_1$-$C_{18}$alkylthio; carboxy; —COOM; $C_1$-$C_{18}$-alkylcarboxyl; aminocarbonyl; or mono- or di-$C_1$-$C_{18}$alkylamino; $C_1$-$C_{10}$acylamino; —COOH;

M is an alkali metal ion;

x is 1 or 2; and y is a number from 2 to 10;

and UV filters selected from ($c_1$) cinnamic acid derivatives; and ($c_2$) dibenzoylmethane derivatives.

$C_1$-$C_{18}$alkyl according to the definition for the radicals of the compound of formula (1) are straight-chain or branched alkyl radicals like methyl, ethyl, n-propyl, isopropyl, n-butyl, sec.butyl, tert.butyl, amyl, isoamyl or tert.amyl, hexyl, 2-ethylhexyl, heptyl, octyl, isooctyl, nonyl, decyl, undecyl, dodecyl, tetradecyl, pentadecyl, hexadecyl, heptadecyl or octadecyl.

$C_1$-$C_{18}$alkyl according to the definition for the radicals of the compound of formula (1) may be substituted by methoxyethyl, ethoxypropyl, 2-ethylhexyl, hydroxyethyl, chloropropyl, N,N-diethylaminopropyl, cyanoethyl, phenethyl, benzyl, p-tert-butylphenethyl, p-tert-octylphenoxyethyl, 3-(2,4-di-tert-amylphenoxy)-propyl, ethoxycarbonylmethyl-2-(2-hydroxyethoxy)ethyl, or 2-furylethyl.

$C_1$-$C_{18}$alkyl according to the definition for the radicals of the compound of formula (1) are for example methoxy, ethoxy, n-propoxy, isopropoxy, n-butoxy, sec.butoxy, tert.butoxy, amyloxy, isoamyloxy or tert.amyloxy, hexyloxy, heptyloxy, octyloxy, isooctyloxy, nonyloxy, decyloxy, undecyloxy, dodecyloxy, tetradecyloxy, pentadecyloxy, hexadecyloxy, heptadecyloxy or octadecyloxy.

$C_6$-$C_{10}$aryl according to the definition for the radicals of the compound of formula (1) is for example naphthyl and preferably phenyl.

The diphenylacrylates ($a_1$) are preferably selected from 2-ethylhexyl 2-cyano-3,3-diphenylacrylate, and 3-(benzofuranyl) 2-cyanoacrylate, and more preferably from 2-ethylhexyl 2-cyano-3,3-diphenylacrylate.

Preferred hydroxyphenyl triazines correspond to formula

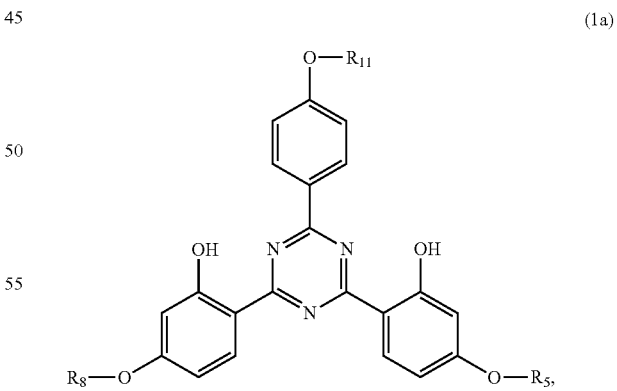

(1a)

wherein $R_5$, $R_8$ and $R_{11}$ independently of one another, are $C_1$-$C_{18}$alkyl.

Most preferred hydroxyphenyl triazine derivatives according to formula (1a) is bis-ethylhexyloxyphenol Methoxyphenyl triazine.

Further preferred hydroxyphenyl triazines correspond to formula (1b)

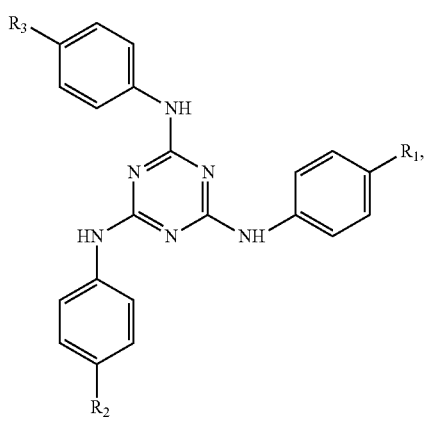

wherein
$R_1$ is —COOR$_6$; or —CO—NHR$_7$;
$R_2$ is —COOR$_9$, or —CO—NHR$_{10}$; and
$R_3$ is —COOR$_{12}$, or —CO—NHR$_{13}$; wherein
$R_6$, $R_7$, $R_9$, $R_{10}$, $R_{12}$ and $R_{13}$ independently of each other are $C_1$-$C_{12}$alkyl, preferably 2-ethylhexyl.

Most preferred hydroxyphenyl triazine derivative according to formula (1a) is Ethylhexyl triazone and dioctyl butamido triazone.

If in formula (2) (for the benzophenone derivatives ($b_1$)) $n_1$ is preferably defined as the number 2,
$R_{16}$ is a $C_1$-$C_{12}$alkylene radical; and
$R_{14}$, $R_{15}$ and A are defined as in formula (2).

Preferably the benzophenone derivative ($b_1$) corresponds to formula (2a)

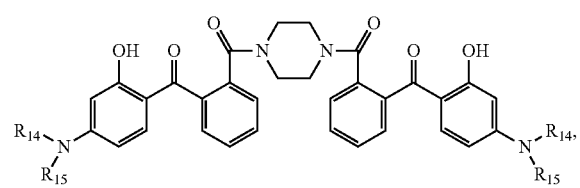

wherein
$R_{14}$ and $R_{15}$ are hydrogen; or $C_1$-$C_5$alkyl.

Most preferably the benzophenone derivative ($b_1$) corresponds to formula

Most preferred benzotriazole derivative according to component ($b_2$) is 2,2'-methanediylbis[6-(2H-benzotriazol-2-yl)-4-(2,4,4-trimethylpentan-2-yl)phenol](Bisotrizole), which corresponds to the compound of formula (3a)

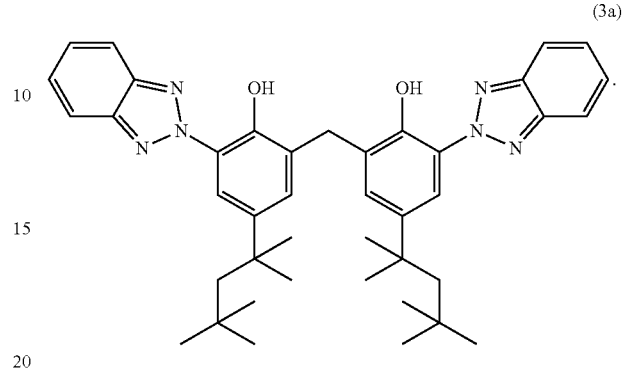

The benzophenone derivatives (b) according to formulas (2) to (4) are preferably used in the micronized state.

Preferred compounds according to component ($b_3$) correspond to the formula (4e)

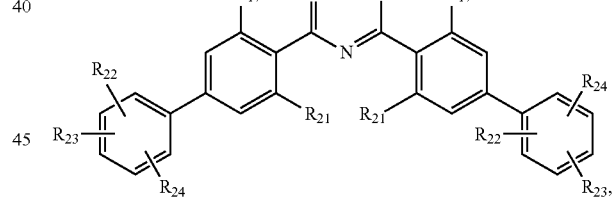

wherein
$R_{17}$, $R_{21}$, $R_{22}$, $R_{23}$ and $R_{24}$ are defined as in formula (4).

More preferred are compounds of formula (4), wherein $R_{17}$ and $R_{21}$ are hydrogen.

(2b)

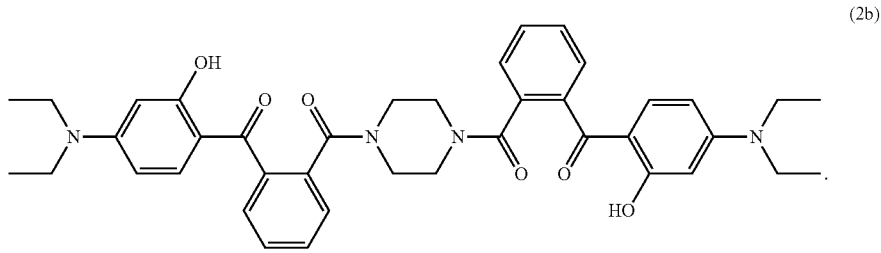 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

Most preferred are the compounds of formual (4d)

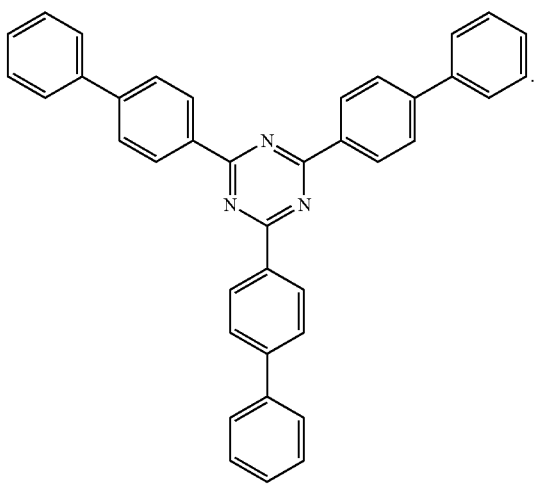

These the organic UV absorbers ($b_1$), ($b_2$) and ($b_3$) are characterized by a poor oil-solubility and a high melting point. They are therefore suitable in particular as UV absorbers in the micronized state.

They may be prepared by any known process suitable for the preparation of microparticles, for example wet-milling, wet-kneading, spray-drying from a suitable solvent, by expansion according to the RESS process (Rapid Expansion of Supercritical Solutions) of supercritical fluids (e.g. $CO_2$, by reprecipitation from suitable solvents, including supercritical fluids (GASR process=Gas Anti-Solvent Recrystallisation/PCA process=Precipitation with Compressed Antisolvents).

As milling apparatus for the preparation of the sparingly soluble micronized organic compounds there may be used, for example, a jet mill, ball mill, vibratory mill or hammer mill, preferably a high-speed mixing mill. Even more preferable mills are modern ball mills; manufacturers of these types of mill are, for example, Netzsch (LMZ mill), Drais (DCP-Viscoflow or Cosmo), Bühler AG (centrifugal mills) or Bachhofer.

Examples of kneading apparatus for the preparation of the micronized organic UV absorbers are typical sigma-blade batch kneaders but also serial batch kneaders (IKA-Werke) or continuous kneaders (Continua from Werner and Pfleiderer).

The grinding of the sparingly soluble organic compounds used in the present invention is preferably carried out with a grinding aid.

The dispersing agent is used as a low molecular weight grinding aid for all the above micronization processes.

Useful anionic, non-ionic or amphoteric surfactants are disclosed below in the sections entitled "specific dispersing agents".

Preferred useful grinding aids for an aqueous dispersion are anionic surfactants with a HLB (Hydrophile-Lipophile Balance) value higher than 8, more preferably higher than 10.

Specific Dispersing Agents

Any conventionally usable anionic, non-ionic or amphoteric surfactants can be used as dispersing agents. Such surfactant systems may comprise for example: carboxylic acids and their salts: alkaline soap of sodium, potassium and ammonium, metallic soap of calcium or magnesium, organic basis soap such as Lauric, myristic, palmitic, stearic and oleic acid etc., alkyl phosphates or phosphoric acid esters, acid phosphate, diethanolamine phosphate, potassium cetyl phosphate, ethoxylated carboxylic acids or polyethyleneglycol esters, PEG-n acylates. Fatty alcohol polyglycolether such as laureth-n, myreth-n, ceteareth-n, steareth-n, oleth-n. fatty acid polyglycolether such as PEG-n stearate, PEG-n oleate, PEG-n cocoate, monoglycerides and polyol esters, $C_{12}$-$C_{22}$ fatty acid mono- and di-esters of addition products of from 1 to 100 mol of ethylene oxide with polyols, fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products, polysorbate-n series, sorbitan esters such as sesquiisostearate, sorbitan, PEG-(6)-isostearate sorbitan, PEG-(10)-sorbitan laurate, PEG-17-dioleate sorbitan, glucose derivatives, C8-C22 alkyl-mono and oligo-glycosides and ethoxylated analogues with glucose being preferred as the sugar component, O/W emulsifiers such as methyl gluceth-20 sesquistearate, sorbitan stearate/sucrose cocoate, methyl glucose sesquistearate, cetearyl alcohol/cetearyl glucoside, W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated paraffins, sulfonated tetrapropylene sulfonate, sodium lauryl sulfates, ammonium and ethanolamine lauryl sulfates, lauryl ether sulfates, sodium laureth sulfates [Texapon N70] or sodium myreth sulfates [Texapon K14S], sulfosuccinates, acetyl isothionates, alkanolamide sulfates, taurines, methyl taurines, imidazole sulfates. Zwitterionic or amphoteric surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, N-alkylaminobetaines.

Examples of suitable mild surfactants as dispersing agents, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Non ionic surfactants such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20 [Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phosphate and glycol stearate and PEG-2 stearate [Sedefos 75], glyceryl stearate and sodium lauryl Sulfate [Teginacid Special]. Cationic acid bases such as cetearyl alcohol and cetrimonium bromide.

Most preferred dispersing agents are sodium alkyl sulfates or sodium alkyl ether sulfates, such as sodium laureth sulfate [Texapon N70 from Cognis] or sodium myreth sulfate [Texapon K14 S from Cognis].

The specific dispersing agents may be used in an amount of, for example, from 1 to 30% by weight, especially from 2 to 20% by weight and preferably from 3 to 10% by weight, based on the total weight of the composition.

Useful solvents are water, brine, (poly-)ethylene glycol, glycerol or cosmetically acceptable oils. Other useful solvents are disclosed below in the sections entitled "Esters of fatty acids", "Natural and synthetic triglycerides, including glyceryl esters and derivatives", "Pearlescent waxes", "Hydrocarbon oils" and "Silicones or siloxanes".

The micronized sparingly soluble organic compounds so obtained usually have an average particle size from 0.02 to 2 micrometres, preferably from 0.03 to 1.5 micrometres and more especially from 0.05 to 1.0 micrometres.

The micronized UV absorbers according to component $(b_1)$, $(b_2)$ and $(b_3)$ of the present invention are used as aqueous dispersions, which comprise 30-60, preferably 35 to 55 parts of the sparingly soluble organic micronized substance according to component $(b_1)$, $(b_2)$ or $(b_3)$ respectively;
2-20, preferably 2 to 20 parts of the dispersing agent;
0.1-1 part, preferably 0.1 to 0.5 parts of a thickening agent (for example xanthan gum); and
20-68 parts of water.

The compounds according to component $(b_1)$, $(b_2)$ or $(b_3)$ have also a stabilizing effect for UV absorbers selected from ethyl hexyl triazine and dioctyl butamido triazone.

The cinnamic acid derivatives $(c_1)$ preferably correspond to the formula

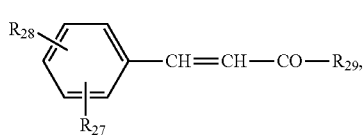

(5)

wherein
$R_{27}$ and $R_{28}$ independently from each other; are hydrogen; hydroxy; $C_1$-$C_5$alkyl; or $C_1$-$C_5$alkoxy; and
$R_{29}$ is $C_1$-$C_5$alkyl.

Most preferred cinnamic acid derivative $(c_1)$ is 2-ethylhexyl 4-methoxycinnamate.

The dibenzoylmethane derivative $(c_2)$ is preferably selected from 4-(tert-butyl)-4'-methoxydibenzoylmethane.

Most preferably, the present invention relates to the use of UV absorbers selected from
$(a_1)$ diphenylacrylates; and
$(a_2)$ hydroxyphenyl triazines of formula (1)
for stabilizing cosmetic compositions comprising
(b) a benzophenone derivative of formula (2); and UV filters selected from
$(c_1)$ cinnamic acid derivatives; and
$(c_2)$ dibenzoylmethane derivatives.

Most preferably, the present invention relates to the use of UV absorbers selected from
$(a_1)$ diphenylacrylates; and
$(a_2)$ hydroxyphenyl triazines of formula (1);
for stabilizing a cosmetic composition comprising
(b) a benzophenone derivative of formula (2b); and
$(c_1)$ a cinnamic acid derivative.

Most preferably, the present invention relates to the use of UV absorbers selected from
$(a_1)$ diphenylacrylates;
$(a_2)$ hydroxyphenyl triazines of formula (1)
for stabilizing a cosmetic composition comprising
(b) a benzophenone derivative of formula (2b); and
$(c_2)$ a dibenzoylmethane derivative.

The present invention also relates to a cosmetic composition comprising
0.1 to 10% b.w. of a diphenylacrylate $(a_1)$ and/or hydroxyphenyl triazine $(a_2)$;
0.1 to 10. % b.w. of an organic UV absorber selected from a benzophenone derivative $(b_1)$; a benzotriazole derivative $(b_2)$ and a triazine derivative $(b_3)$; and
0.1 to 10% b.w. of a cinnamic acid derivative $(c_1)$ and/or a dibenzoylmethane derivative $(c_2)$;
wherein the UV filters $(a_1)$, $(a_2)$, $(b_1)$, $(b_2)$, $(b_3)$, $(c_1)$ and $(c_2)$ are defined as in claim 1.

Preferred are also cosmetic compositions comprising
0.1 to 10% b.w. of a diphenylacrylate $(a_1)$ and/or hydroxyphenyl triazine $(a_2)$;
0.1 to 10. % b.w. of a benzophenone derivative $(b_1)$; and
0.1 to 10% b.w. of a cinnamic acid derivative $(c_1)$ and/or a dibenzoylmethane derivative $(c_2)$;
wherein the UV filters $(a_1)$, $(a_2)$, $(b_1)$, $(c_1)$ and $(c_2)$ are defined as in claim 1.

The present invention also relates to the Use of UV absorbers selected from
$(b_1)$ a benzophenone derivative of formula (2);
$(b_2)$ a benzotriazole derivative of formula (3); and
$(b_3)$ a triazine derivative of formula (4)
for stabilizing cosmetic compositions comprising
$(a_2)$ a hydroxyphenyl triazine of formula (1), wherein
the compounds of formulas (1), (2), (3) and (4) are defined as in claim 1.

The cosmetic formulations or pharmaceutical compositions according to the present invention may additionally contain one or more than one further UV filter as listed in Tables 1 and 2.

TABLE 1

Suitable UV filter substances which can be additionally used with the UV absorbers according to the present invention p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative;
3-imidazol-4-yl acrylic acid and esters;
benzofuran derivatives, especially 2-(p-amino phenyl)benzofuran derivatives, described in EP-A-582 189, US-A-5 338 539, US-A-5 518 713 and EP-A-613 893;
polymeric UV absorbers, for example the benzylidene malonate derivatives described in EP-A-709 080;
camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
benzotriazole compounds, for example 2,2'-methylene-bis(6-(2H-benzotriazol-2-yl)-4-(1,1,3,3-tetramethylbutyl)-phenol;
trianilino-s-triazine derivatives, for example 2,4,6-trianiline-(p-carbo-2'-ethyl-1'-oxy)-1,3,5-triazine and the UV absorbers disclosed in US-A-5 332 568, EP-A-517 104, EP-A-507 691, WO 93/17002 and EP-A-570 838;
2-phenylbenzimidazole-5-sulfonic acid and salts thereof;
menthyl o-aminobenzoates;
inorganic particulate sunscreens coated or not such as titanium dioxide, zinc oxide, iron oxides, mica, MnO, $Fe_2O_3$, $Ce_2O_3$, $Al_2O_3$, $ZrO_2$. (surface coatings: polymethylmethacrylate, methicone (methylhydrogenpolysiloxane as described in CAS 9004-73-3), dimethicone, isopropyl titanium triisostearate (as described in CAS 61417-49-0), metal soaps as magnesium stearate (as described in CAS 4086-70-8), perfluoroalcohol phosphate as C9-15 fluoroalcohol phosphate (as described in CAS 74499-44-8; JP 5-86984, JP 4-330007)). The primary particle size is an average of 5 nm-35 nm and the particle size in dispersion is in the range of 100 nm-300 nm.
aminohydroxy-benzophenone derivatives disclosed in DE 10011317, EP 1133980 and EP 1046391
phenyl-benzimidazole derivatives as disclosed in EP 1167358

TABLE 2

Suitable UV filter substances and adjuvants which can be additionally used with the UV absorbers according to the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | Methyl N,N,N-trimethyl-4-[(4,7,7-trimethyl-3-oxobicyclo[2,2,1]-hept-2-ylidene)methyl]anilinium sulphate; Mexoryl SO | 52793-97-2 |
| 12 | 3,3,5-Trimethyl cyclohexyl-2-hydroxy benzoate; homosalate | 118-56-9 |
| 13 | Menthyl-o-aminobenzoate | 134-09-8 |
| 14 | Menthyl salicylate | 89-46-3 |
| 15 | 2-ethylhexyl 4-(dimethylamino)benzoate | 21245-02-3 |
| 16 | 2-ethylhexyl salicylate | 118-60-5 |
| 17 | 4-aminobenzoic acid | 150-13-0 |
| 18 | Benzoic acid, 4-amino-, ethyl ester, polymer with oxirane | 113010-52-9 |
| 19 | 2-phenyl-1H-benzimidazole-5-sulphonic acid; phenylbenzimidazolsulfonic acid | 27503-81-7 |
| 20 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 21 | Triethanolamine salicylate | 2174-16-5 |
| 22 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 23 | Titanium Dioxide | 13463-67-7 |
| 24 | Zinc oxide | 1314-13-2 |
| 25 | 1H-Benzimidazole-4,6-disulfonic acid, 2,2'-(1,4-phenylene)bis-, disodium salt | 180898-37-7 |
| 26 | Benzoic acid, 4,4'-[[6-[[[(1,1-dimethylethyl)amino]carbonyl]-phenyl]amino]1,3,5-triazine-2,4-diyl]diimino]bis-, bis(2-ethyl-hexyl)ester; diethylhexyl butamido triazone; Uvasorb HEB | 154702-15-5 |
| 27 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 155633-54-8 |
| 28 | Dimethicodiethylbenzalmalonate; Polysilicone 15; Parsol SLX | 207574-74-1 |
| 29 | Benzenesulfonic acid, 3-(2H-benzotriazol-2-yl)-4-hydroxy-5-(1-methylpropyl)-, monosodium salt; Tinogard HS | 92484-48-5 |
| 30 | 1-Dodecanaminium, N-[3-[[4-(dimethylamino)benzoyl]amino]-propyl]N,N-dimethyl-, salt with 4-methylbenzenesulfonic acid (1:1); Escalol HP610 | 156679-41-3 |
| 31 | 1-Propanaminium, N,N,N-trimethyl-3-[(1-oxo-3-phenyl-2-propenyl)amino]-, chloride | 177190-98-6 |
| 32 | 1H-Benzimidazole-4,6-disulfonic acid, 2,2'-(1,4-phenylene)bis- | 170864-82-1 |
| 33 | 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 34 | 2-Propenoic acid, 3-(1H-imidazol-4-yl)- | 104-98-3 |
| 35 | Benzoic acid, 2-hydroxy-, [4-(1-methylethyl)phenyl] methyl ester | 94134-93-7 |
| 36 | 1,2,3-Propanetriol, 1-(4-aminobenzoate); glyceryl PABA | 136-44-7 |
| 37 | Benzene acetic acid, 3,4-dimethoxy-a-oxo- | 4732-70-1 |
| 38 | 2-Propenoic acid, 2-cyano-3,3-diphenyl-, ethyl ester | 5232-99-5 |
| 39 | Anthralinic acid, p-menth-3-yl ester | 134-09-8 |
| 40 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |
| 41 | 1,3,5-Triazine-2,4,6-triamine, N,N'-bis[4-[5-(1,1-dimethylpropyl)-2-benzoxazolyl]phenyl]-N"-(2-ethylhexyl)- or Uvasorb K2A | 288254-16-0 |
| 42 | sterols (cholesterol, lanosterol, phytosterols), as described in WO0341675 | |
| 43 | mycosporines and/or mycosporine-like amino acids as described in WO2002039974, e.g. Helioguard 365 from Milbelle AG, isolated mycosporine like amino acids from the red alga porphyra umbilicalis (INCI: *Porphyra Umbilicalis*) that are encapsulated into liposomes,) | |
| 44 | alpha-lipoic-acid as described in DE 10229995 | |
| 45 | synthetic organic polymers as described in EP 1371358, [0033]-[0041] | |
| 46 | phyllosilicates as described in EP 1371357 [0034]-[0037] | |
| 47 | silica compounds as described in EP1371356, [0033]-[0041] | |
| 48 | inorganic particles as described in DE10138496 [0043]-[0055] | |
| 49 | latex particles as described in DE10138496 [0027]-[0040] | |
| 50 | 1H-Benzimidazole-4,6-disulfonic acid, 2,2'-(1,4-phenylene)bis-, disodium salt; Bisimidazylate; Neo Heliopan APC | 180898-37-7 |

TABLE 2-continued

Suitable UV filter substances and adjuvants which can be additionally used with the UV absorbers according to the present invention

| No. | Chemical Name | CAS No. |
|---|---|---|
| 51 | (E- or Z configuration) | |
| 52 | (E- or Z configuration) | |
| 53 | | |
| 54 | | |

The cosmetic or pharmaceutical preparations can be prepared by physically mixing the UV absorbers ($a_1$) ($a_2$), ($b_1$) ($b_2$), ($b_3$), and ($c_1$) and ($c_2$) and optionally further UV absorbers with the adjuvant using customary methods, for example by simply stirring together the individual components.

Cosmetic or pharmaceutical preparations contain from 0.05-40% by weight, based on the total weight of the composition, of the UV absorber mixture of the present invention.

The UV absorber mixture according to the present invention is useful to protect skin, hair and/or natural or artificial hair color.

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctylstearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Other Adjuvants alpha glucosylrutin (CAS No. 130603-71-3), 2-butyloctyl o-hydroxybenzoate (CAS No. 190085-41-7), vitamin E (CAS No. 1406-18-4), vitamin E acetate (CAS No. 58-95-7), diethylhexyl 2,6-naphthalate, di-n-butyl adipate, di(2-ethylhexyl)-adipate, di(2-ethylhexyl)-succinate and diisotridecyl acetate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups, or iminodisuccinic acid and iminodisuccinic acid salts [CAS 7408-20-0] or latex particles, aloe vera, chamomile, ginko biloba, ginseng, coenzyme Q10, laminaria ochroleuca extract, magnolia oborata extract, melalenca alternifolia leaf oil, rubus idaeus seed oil, vaccinium macrocarpon seed oil, pumpkin seed extract, pumpkin seed oil, grape seed extract, carnosine, alpha-arbutin, madecassoside, termino-laside, tetrahydrocurcuminoids (THC), mycosporines, mycosporine like amino acids from the red alga porphyra umbilicalis, mycosporine-like amino acids (as described in WO2002039974), cis-9-octadecenedioic acid, lipoic acid, laurimino dipropiomic acid tocopheryl phosphates (LDTP), microcrystalline cellulose (MCC), polycarbonates as described in WO 0341676, sterols (cholesterol, lanosterol, phytosterols), as described in WO0341675 and linear poly-alpha-glucans as described in U.S. Pat. No. 6,616,935

Natural or Synthetic Triglycerides Including Glyceryl Esters and Derivatives

Di- or tri-glycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates.

A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carboxylic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated paraffins, sulfonated tetrapropylene sulfonate, sodium lauryl sulfates, ammonium and ethanolamine lauryl sulfates, lauryl ether sulfates, sodium laureth sulfates, sulfosuccinates, acetyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chloride, cetyl pyridinium bromide, quaternary ammonium such as cetyltrimethylbroide ammonium bromide (CTBA), stearylalkonium. Amide derivatives, alkanolamides such as acylamide DEA, ethoxylated amides such as PEG-n acylamide, oxydeamide. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block (oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p 250-251.

Nonionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20 [Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and steareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phosphate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Adjuvants and Additives

The cosmetic/pharmaceutical preparations, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants, bacteria-inhibiting agents and the like.

Super-fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicium dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropylmethylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80(steareth-10 allyl ether/acrylates copolymer), Salcare SC81 (acrylates copolymer), Salcare SC91 and Salcare AST (sodium acrylates copolymer/-PPG-1 trideceth-6), sepigel 305 (polyacrylamide/laureth-7), Simulgel NS and Simulgel EG (hydroxyethyl acrylate/sodium acryloyldimethyl taurate copolymer), Stabilen 30 (acrylates/vinyl isodecanoate crosspolymer), Pemulen TR-1 (acrylates/C10-30 alkyl acrylate crosspolymer), Luvigel EM (sodium acrylates copolymer), Aculyn 28 (acrylates/beheneth-25 methacrylate copolymer), etc.

Polymers

Suitable cationic polymers are, for example, cationic cellulose derivatives, for example a quaternized hydroxymethyl cellulose obtainable under the name Polymer JR 400 from Amerchol, cationic starches, copolymers of diallylammonium salts and acrylamides, quarternised vinylpyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat® L/Grünau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and poly-acrylic acids crosslinked with polyols, acrylamidopropyl-trimethylammonium chloride/acrylate copolymers, octyl acrylamide/methyl methacrylatetert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients there come into consideration, for example, antiperspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl\times2.5H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2,4-dichlorophenoxy)-phenol (Triclosan, Irgasan, Ciba Specialty Chemicals Inc.) has also proved especially effective.

Anti-dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Antioxidants

In addition to the primary light-protective substances it is also possible to use secondary light-protective substances of the antioxidant kind that interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, heptathionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned.

Further synthetic and natural antioxidants are listed e.g. in WO 0025731:

Structures 1-3 (page 2), structure 4 (page 6), structures 5-6 (page 7) and compounds 7-33 (page 8-14).

The amount of antioxidants present is usually from 0.001 to 30% by weight, preferably from 0.01 to 3% by weight, based on the weight of the UV absorber of formula (1).

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glycerine, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives

Suitable preservatives include, for example, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo—A short textbook of cosmetology, Chapter 7, Table 7-2, 7-3, 7-4 and 7-5, p 210-219.

Bacteria-inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petit-grain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenyl acetic acid, geranyl acetate, benzyl acetate, rose oxide, romillat, irotyl and floramat alone or in admixture with one another.

Colorants

There may be used as colorants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colorants are usually used in concentrations of from 0.001 to 0.1% by weight, based on the total mixture.

Other Adjuvants

It is furthermore possible for the cosmetic preparations to contain, as adjuvants, anti-foams, such as silicones, structurants, such as maleic acid, solubilizers, such as ethylene glycol, propylene glycol, glycerol or diethylene glycol, opacifiers, such as latex, styrene/PVP or styrene/acrylamide copolymers, complexing agents, such as EDTA, NTA, alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

Polymeric Beads or Hollow Spheres as SPF Enhancers

The combination of the UV-absorbers and UV-absorber combinations, listed above, with SPF enhancers, such as non-active ingredients like Styrene/acrylates copolymer, silica beads, spheroidal magnesium silicate, crosslinked Polymethylmethacrylates (PMMA; Micopearl M305 Seppic), can maximize better the UV protection of the sun products. Holosphere additives (Sunspheres® ISP, Silica Shells Kobo.) deflect radiation and the effective path length of the photon is therefore increased. (EP0893119). Some beads, as mentioned previously, provide a soft feel during spreading. Moreover, the optical activity of such beads, e.g. Micropearl M305, cans modulate skin shine by eliminating reflection phenomena and indirectly may scatter the UV light.

Cosmetic or Pharmaceutical Preparations

Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eye shadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de perfume, perfume de toilette, perfume), perfume oils or perfume creams;

cosmetic hair-treatment preparations, e.g. hair-washing preparations in the form of shampoos and conditioners, hair-care preparations, e.g. pre-treatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellant gas or pump-action spray) or an aerosol, in the form of a foam, or in the form of a paste.

Of special importance as cosmetic preparations for the skin are light-protective preparations, such as sun milks, lotions, creams, oils, sun blocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pre-treatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of the aqueous dispersion as defined in claim 1, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

$a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyl dimethyl-2-hydroxyethylammonium chloride or Quaternium 80 is added;

$a_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl dimethyl-2-hydroxyethylammonium chloride or Quaternium 80 is added;

b) quat-doped solutions of the UV absorber according to the invention in butyl triglycol and tributyl citrate;

c) mixtures or solutions of the UV absorber according to the invention with n-alkylpyrrolidone.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

Examples of Cosmetic and Pharmaceutical Preparations (X=Preferred Combinations)

| O/W systems: | | | | | | | | |
|---|---|---|---|---|---|---|---|---|
| Ingredients | 1 | 2 | 3 | 4 | 5 | 6 | 7 | 8 |
| Potassium Cetyl Phosphate 2%-5% | X | | | | | | | |
| Cetearyl Alcohol/Dicetyl Phosphate/Ceteth-10 Phosphate 2%-6% | | X | | | | | | |
| Sodium Stearyl Phtalamate 1%-2% | | | X | | | | | |
| Cetearyl Alcohol/Behentrimonium Methosulfate 1%-5% | | | | X | | | | |
| Quaternium-32 1%-5% | | | | | X | | | |
| Dimethicone copolyol/Caprylic/Capric Triglyceride (1%-4%) | | | | | | X | | |
| Steareth-2/Steareth-21 2%-5% | | | | | | | X | |
| Polyglyceryl Methyl Glucose Distearate 1%-4% | | | | | | | | X |
| Lipophilic emollient/dispersant oil 15%-20% | X | X | X | X | X | X | X | X |
| Fatty Alcohols and/or Waxes 1%-5% | X | X | X | X | X | X | X | X |
| Thickeners (water swellable thickeners) 0.5%-1.5% | X | X | X | X | X | X | X | X |
| Preservatives 0.5%-1% | X | X | X | X | X | X | X | X |
| Chelating agents (such as EDTA) 0%-0.2% | X | X | X | X | X | X | X | X |
| Antioxidants 0.05%-0.2% | X | X | X | X | X | X | X | X |
| Water deionizer Qs 100% | X | X | X | X | X | X | X | X |
| Perfume oils 0.1%-0.4% | X | X | X | X | X | X | X | X |
| Cosmetic composition according to the present invention 0.1%-20% | X | X | X | X | X | X | X | X |
| UV-absorber as described in Table 1 and 2 0%-30% | X | X | X | X | X | X | X | X |

| W/O systems | | | | | |
|---|---|---|---|---|---|
| Ingredients | 1 | 2 | 3 | 4 | 5 |
| Polyglyceryl-2 Dipolyhydroxystearate 2%-4% | X | X | X | X | X |
| PEG-30 Dipolyhydroxystearate 2%-4% | | X | | | |
| Rapeseed Oil Sorbitol Esters 1%-5% | | | X | | |
| PEG-45/Dodecyl Glycol Copolymer 1%-5% | | | | X | |
| Sorbitan Oleate/Polycerol-3 ricinoleate 1%-5% | | | | | X |
| Lipophilic emollient/dispersant oil 10%-20% | X | X | X | X | X |
| Fatty Alcohols and/or Waxes 10%-15% | X | X | X | X | X |
| Electrolytes (NaCl, MgSO$_4$) 0.5%-1% | X | X | X | X | X |
| Polyol phase (Propylene glycol, glycerin) 1%-8% | X | X | X | X | X |
| Preservatives 0.3%-0.8% | X | X | X | X | X |
| Perfume oils 0.1%-0.4% | X | X | X | X | X |
| Chelating agents (such as EDTA) 0%-0.2% | X | X | X | X | X |
| Antioxidants 0.05%-0.2% | X | X | X | X | X |
| Water deionized Qs 100% | X | X | X | X | X |
| Cosmetic composition according to the present invention 0.1%-20% | X | X | X | X | X |
| UV-absorber as described in Table 1 and 2 0%-30%. | X | X | X | X | X |

| W/Silicone systems | | | | |
|---|---|---|---|---|
| Ingredients | 1 | 2 | 3 | 4 |
| Dimethicone Copolyol/Cyclomethicone 5%-10% | X | | X | |
| Laurylmethicone Copolyol 5%-10% | | X | | X |
| Cyclopentasiloxane 15%-25% | X | | | X |
| Dimethicone 15%-25% | | X | X | |
| Dimethicone/Vinyldimethicone Crosspolymer 1%-10% | X | X | X | X |
| Humectant/polyols (Propylene glycol, glycerin . . .) 2%-8% | X | X | X | X |
| Chelating agents (such as EDTA) 0%-0.2% | X | X | X | X |
| Antioxidants 0.05%-0.2% | X | X | X | X |
| Preservatives 0.3%-0.8% | X | X | X | X |
| Perfume oils 0.1%-0.4% | X | X | X | X |
| Water deionized Qs 100% | X | X | X | X |
| Cosmetic composition according to the present invention 0.1%-20% | X | X | X | X |
| UV-absorber as described in Table 1 and 2 0%-30% | X | X | X | X |

| Multiple emulsions | | | | | | | | | | | | |
|---|---|---|---|---|---|---|---|---|---|---|---|---|
| Ingredients | 1 | 2 | 3 | 4 | 5 | 6 | 7 | 8 | 9 | 10 | 11 | 12 |
| PEG-30 Dipolyhydroxystearate (2%-6%) | X | | | | | | | | | X | | X |
| Cetyl Dimethicone Copolyol 1%-3% | | X | | | | | | | X | | | |
| PEG-30 Dipolyhydroxystearate/Steareth-2/Steareth-21 4%-6% | | | X | | | | | X | | | | |
| Polyglyceryl-2 Dipolyhydroxystearate 1%-3% | | | | X | | | X | | | | | |
| Polyglyceryl-6 Ricinoleate 1%-3% | | | | | X | X | | | | | X | |
| Oil phase 15%-30% | | | | | | | | | | | | |
| Fatty acid esters | X | X | X | X | X | | | | | | X | X |
| Natural and synthetic Triglycerides | | | | | | X | X | X | X | X | X | X |
| Hydrocarbon oils | X | X | X | X | | | | | | | X | X |
| Silicone oils | | | | | | X | X | X | X | X | X | X |
| Preservatives 0.3%-0.8% | X | X | X | X | X | X | X | X | X | X | X | X |

| Multiple emulsions | | | | | | | | | | | | |
|---|---|---|---|---|---|---|---|---|---|---|---|---|
| Ingredients | 1 | 2 | 3 | 4 | 5 | 6 | 7 | 8 | 9 | 10 | 11 | 12 |
| Water Deioniz. qs 100% | X | X | X | X | X | X | X | X | X | X | X | X |
| Sorbitan Stearate/Sucrose Cocoate 3%-7% | X | | | | | | | X | | | | X |
| Sucrose Laurate 3%-7% | | X | | | | X | | | X | | X | |
| Poloxamer 407 3%-7% | | | X | | | X | | | X | | | |
| Polyoxyethylene(20)Sorbate Monoleate 3%-5% | | | | X | X | | | | | X | | |
| Primary emulsion W1/O 50% | X | X | X | X | X | X | X | X | X | X | X | X |
| Thickeners (water swellable polymers) 0.3%-1% | X | X | X | X | X | X | X | X | X | X | X | X |
| Water deionized Qs 100% | X | X | X | X | X | X | X | X | X | X | X | X |
| Perfume oils 0.1%-0.4% | X | X | X | X | X | X | X | X | X | X | X | X |
| Cosmetic composition according to the present invention 0.1%-20% | X | X | X | X | X | X | X | X | X | X | X | X |
| UV-absorber as described in Table 1 and 2 0%-30% | X | X | X | X | X | X | X | X | X | X | X | X |

| O1/W/O2 emulsions | | | | | | | | |
|---|---|---|---|---|---|---|---|---|
| Ingredients | 1 | 2 | 3 | 4 | 5 | 6 | 7 | 8 |
| Primary emulsion O1/W | | | | | | | | |
| PEG-60 Hydrogenated Castor Oil 25% | X | | | X | X | | | X |
| Steareth-25 25% | | X | X | | | X | X | |
| Oil phase 75% | | | | | | | | |
| Fatty acid esters | X | | X | | | | | |
| Natural and synthetic Triglycerides | | X | | X | | | | |
| Hydrocarbon oils | | | | | X | | X | |
| Silicone oils | | | | | | X | | X |
| Preservatives 0.3%-0.8% | X | X | X | X | X | X | X | X |
| Water deionized Qs 100% | X | X | X | X | X | X | X | X |
| Non ionic multifunctional W/O emulsifier 2%-5% | X | X | X | X | X | X | X | X |
| Waxes 1%-5% | X | X | X | X | X | X | X | X |
| Oil phase 20%-30% | X | X | X | X | X | X | X | X |
| Silicone oils | | | | | | | | |
| Primary emulsion O1/W 15% | X | X | X | X | X | X | X | X |
| Electrolytes (NaCl, MgSO4) 0.1%-0.5% | X | X | X | X | X | X | X | X |
| Water deionized Qs 100% | X | X | X | X | X | X | X | X |
| Perfume oils 0.1%-0.4% | X | X | X | X | X | X | X | X |
| Cosmetic composition according to the present invention 0,1%-20% | X | X | X | X | X | X | X | X |
| UV-absorber as described in Table 1 and 2 0%-30% | X | X | X | X | X | X | X | X |

| Microemulsions | | | | | | | | | | |
|---|---|---|---|---|---|---|---|---|---|---|
| Ingredients | 1 | 2 | 3 | 4 | 5 | 6 | 7 | 8 | 9 | 10 |
| PEG-8 Caprylic/Capric Glycerides 10%-25% | X | | | X | X | | | X | X | |
| PPG-5-ceteth-20 10%-25% | | X | X | | | X | X | | | X |
| Polyglyceryl-6 Isostearate 5%-15% | X | | X | | | | | | | |
| Polyglyceryl-3 Diisostearate 5%-15% | | X | | X | | | | | | |
| Polyglyceryl-6 Dioleate 5%-15% | | | | | X | | X | | | |
| PPG-10 Cetyl Ether 5%-15% | | | | | | X | | X | | |
| Ethoxydiglycol 5%-15% | | | | | | | | | X | X |
| Oil phase 10%-80% | X | X | X | X | X | X | X | X | X | X |
| Isostearyl Benzoate | X | X | X | X | X | X | X | X | X | X |
| Isostearyl Isostearate | X | X | X | X | X | X | X | X | X | X |
| PEG-7 Glyceryl Cocoate | X | X | X | X | X | X | X | X | X | X |
| Cyclomethicone | X | X | X | X | X | X | X | X | X | X |
| Polyalcohols/Humectants 1%-10% | X | X | X | X | X | X | X | X | X | X |
| Preservatives 0.3-0.8% | X | X | X | X | X | X | X | X | X | X |
| Perfume oils 0.1%-0.4% | X | X | X | X | X | X | X | X | X | X |
| Water Deioniz. qs 100% | X | X | X | X | X | X | X | X | X | X |
| Cosmetic composition according to the present invention 0.1%-20% | X | X | X | X | X | X | X | X | X | X |
| UV-absorber as described in Table 1 and 2 0%-30% | X | X | X | X | X | X | X | X | X | X |

| O/W Spray emulsions | | | | | | |
|---|---|---|---|---|---|---|
| Ingredients | 1 | 2 | 3 | 4 | 5 | 6 |
| Alkyl Phosphates 0.1%-5% | X | | | X | X | |
| Glucosidic derivatives 0.1%-5% | | X | X | | | X |
| Solubilisants | | | | | | |
| Ethoxylated Glyceryl ethers 0.1%-1% | X | | X | | | |
| Polysorbates 0.1%-1% | | X | | X | | |
| Ethoxylated Oleyl ethers 0.1%-1% | | | | | X | X |
| PVP/VA Copolymer 1%-10% | X | | X | | X | |
| PVM/MA Copolymer 1%-10% | | X | | X | | X |
| Oil phase 5%-20% | X | X | X | X | X | X |
| Natural oils (Meadowfoam, Jojoba, *Macadamia* . . .) | X | X | X | X | X | X |
| Fatty acids esters | X | X | X | X | X | X |
| Mineral oils | X | X | X | X | X | X |
| Silicone oils | X | X | X | X | X | X |
| Alcohol 0%-50% | X | X | X | X | X | X |
| Thickeners 0.1%-0.5% | X | X | X | X | X | X |
| Polyacrylates | X | X | X | X | X | X |
| Aluminum/Magnesium Silicates | X | X | X | X | X | X |
| Gums | X | X | X | X | X | X |
| Neutralizing agents 0%-1% | X | X | X | X | X | X |
| Polyalcohols/Humectants 1%-5% | X | X | X | X | X | X |
| Chelating agents (such as EDTA) 0%-0.2% | X | X | X | X | X | X |
| Antioxidants 0.05%-0.2% | X | X | X | X | X | X |
| Water Deioniz. qs 100% | X | X | X | X | X | X |
| Perfume oils 0.1%-0.5% | X | X | X | X | X | X |
| Preservatives 0.4%-1% | X | X | X | X | X | X |
| Cosmetic composition according to the present invention 0.1%-20% | X | X | X | X | X | X |
| UV-absorber as described in Table 1 and 2 0%-30% | X | X | X | X | X | X |

| G - Aqueous | | | | | | | | | | | | |
|---|---|---|---|---|---|---|---|---|---|---|---|---|
| Ingredients | 1 | 2 | 3 | 4 | 5 | 6 | 7 | 8 | 9 | 10 | 11 | 12 |
| Thickeners | | | | | | | | | | | | |
| Natural Thickener 1%-5% | X | | | | X | X | | | | | | X |
| Semi-synthetic Thickener 1%-5% | | X | | | X | | | X | | | X | |
| Synthetic Thickener 0.3%-1.3% | | | X | X | | | | | X | X | | |
| Neutralizing Agents 0.5%-1.5% | X | X | X | X | X | X | X | X | X | X | X | X |
| Polyols - Humectants 5%-50% | X | X | X | X | X | X | X | X | X | X | X | X |
| Polyquaternium series 1%-5% | X | X | X | | | | X | X | X | | | |
| PVM/MA Copolymer 1%-5% | | | | X | X | X | | | | X | X | X |
| Preservatives 0.5%-1% | X | X | X | X | X | X | X | X | X | X | X | X |
| Chelating Agents (as EDTA) <0.1% | X | X | X | X | X | X | X | X | X | X | X | X |
| Water Deioniz. qs 100% | X | X | X | X | X | X | X | X | X | X | X | X |
| Perfume oils 0.05%-0.4% | X | X | X | X | X | X | X | X | X | X | X | X |
| Ethoxylated Glyceryl ethers 0.1%-5% | X | X | X | | | | | | | | | |
| Polysorbates 0.1%-5% | | | | X | X | X | | | | | | |
| Ethoxylated Oleyl ethers 0.1%-5% | | | | | | | X | X | | X | X | X |
| Cosmetic composition according to the present invention 0.1%-20% | X | X | X | X | X | X | X | X | X | X | X | X |
| UV-absorber as described in Table 1 and 2 0%-30% | X | X | X | X | X | X | X | X | X | X | X | X |

| Oleogels | | | | | | | | | | |
|---|---|---|---|---|---|---|---|---|---|---|
| Ingredients | 1 | 2 | 3 | 4 | 5 | 6 | 7 | 8 | 9 | 10 |
| Hydrogenated Lecithin 1%-10% | X | | | | | | | | | X |
| Silica Dimethyl Silylate 1%-10% | | X | | | | | | | X | |
| Silica 1%-5% | | | X | | | | | X | | |
| $C_{24-28}$ Alkyl Dimethicone 1%-5% | | | | | X | | X | | | |
| Aluminum or Magnesium Stearate 1%-5% | | | | | | X | X | | | |
| Polyols - Humectants 5%-70% | X | X | X | X | X | X | X | X | X | X |
| Oil phase 20% - 90% | | | | | | | | | | |
| Dicaprylyl Ether | X | | | | | X | | X | | |
| Phenyl Trimethicone | | X | | | | | | X | | |
| Hydrogenated Polyisobutene | | | | X | | | | | | |
| Isopropyl Isostearate | | | | | X | | | | X | |
| Oleogel basis (Mineral oil and hydrogenated Butylene/Ethylene or Ethylene/Propylene Styrene Copolymer) | | | | | | X | | | | X |
| Siliconewax 1%-10% | X | X | X | X | X | X | X | X | X | X |
| Dimethiconol Behenate | X | X | X | X | X | X | X | X | X | X |
| Dimethiconol Stearate | X | X | X | X | X | X | X | X | X | X |
| Perfume oils 0.1%-0.5% | X | X | X | X | X | X | X | X | X | X |
| Antioxidants 0.05%-0.2% | X | X | X | X | X | X | X | X | X | X |
| Cosmetic composition according to the present invention 0.1%-20% | X | X | X | X | X | X | X | X | X | X |
| UV-absorber as described in Table 1 and 2 0%-30%) | X | X | X | X | X | X | X | X | X | X |

Light/dry cosmetic oils

| Ingredients | 1 | 2 | 3 | 4 |
|---|---|---|---|---|
| Hydrocarbon oils 30%-70% | X |   |   | X |
| Fatty acid esters branched or not 10%-50% |   | X | X |   |
| Silicon/Siloxanes 0%-10% | X |   | X |   |
| Perfluorinated oils and Perfluoroethers 0%-10% |   | X |   | X |
| Viscosifying agents 0%-10% | X | X | X | X |
| Esters of long chain acids and alcohols 0%-2% | X | X | X | X |
| Antioxidants 0.1%-1% | X | X | X | X |
| Solubilisants/dispersing agents 0%-5% | X | X | X | X |
| Perfume oils 0.1%-0.5% | X | X | X | X |
| Cosmetic composition according to the present invention 0.1%-20% | X | X | X | X |
| UV-absorber as described in Table 1 and 2 0%-30% | X | X | X | X |

Foaming/mousse products

| Ingredients | 1 |
|---|---|
| SD Alcohol 40 0%-8% | X |
| Propellant 8%-15% | X |
| Nonionic Emulsifier/Surfactant 0.5%-3% | X |
| Corrosion Inhibitor 0%-1% | X |
| Perfume oils 0.1%-0.5% | X |
| Preservatives 0.1%-1% | X |
| Miscellaneous 0%-1% | X |
| Cosmetic composition according to the present invention 0.1%-20% | X |
| UV-absorber as described in Table 1 and 2 0%-30% | X |

Stick products

| Ingredients | 1 |
|---|---|
| Waxes 15%-30% | X |
| Natural and silicone oils 20%-75% | X |
| Lanoline derivatives 5%->50% | X |
| Esters of lanolin | x |
| Acetylated lanolin | x |
| Lanolin oil | x |
| Colorants and pigments 10%-15% | X |
| Antioxidants 0.1%-0.8% | X |
| Perfume oils 0.1%-2% | X |
| Preservatives 0.1%-0.7% | X |
| Cosmetic composition according to the present invention 0.1%-20% | X |
| UV-absorber as described in Table 1 and 2 0%-30% | X |

Liquid and compact

| Ingredients | 1 | 2 |
|---|---|---|
| Liquid foundation |   |   |
| Powder phase 10%-15% | X |   |
| Oil phase 30%-40%; 75% (only for anhydrous form) | X |   |
| Thickener/suspending agents 1%-5% | X |   |
| Film forming polymers 1%-2% | X |   |
| Antioxidants 0.1%-1% | X |   |
| Perfume oils 0.1%-0.5% | X |   |
| Preservatives 0.1%-0.8% | X |   |
| Water deionized Qs 100% | X |   |
| Compact powder |   |   |
| Powder phase 15%-50% |   | X |
| Oil phase 15%-50% |   | X |
| Polyol phase 5%-15% |   | X |
| Antioxidants 0.1%-1% |   | X |
| Perfume oils 0.1%-0.5% |   | X |
| Preservatives 0.1%-0.8% |   | X |
| For the two product forms |   |   |
| Cosmetic composition according to the present invention 0.1%-20% | X | X |
| UV-absorber as described in Table 1 and 2 0%-30% | X | X |

Conditioning Shampoos

| Ingredients | 1 |
|---|---|
| Primary surfactants (listed previously) 5%-10% | X |
| Secondary surfactants (listed previously) 5%-15% | X |
| Foam Stabilizers (listed previously) 0%-5% | X |
| Water deionized 40%-70% | X |
| Actives 0-10% | X |
| Conditioners | x |
| Refatting agents | x |
| Moisturizing agents | x |
| Thickeners/Rheology modifiers 0%-3% | X |
| Humectants 0%-2% | X |
| PH adjusting agents 0%-1% | X |
| Preservatives 0.05%-1% | X |
| Perfume oils 0.1%-1% | X |
| Antioxidants 0.05%-0.20% | X |
| Chelating Agents (EDTA) 0%-0.2% | X |
| Opacifying agents 0%-2% | X |
| Cosmetic composition according to the present invention 0.1%-20% | X |
| UV-absorber as described in Table 1 and 2 0%-30% | X |

O/W FORMULATION
Anionic System emulsifier

| | Sun Milk INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | C12-15 Alkyl Benzoate | 2.00 | 2.00 | 2.00 | 2.00 | 2.00 | 2.00 | 2.00 | 2.00 | 2.00 |
| | Phenethyl Benzoate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | Diethylhexyl Succinate | 1.00 | 1.00 | 1.00 | 1.00 | 1.00 | 1.00 | 1.00 | 1.00 | 1.00 |
| | Isohexadecane | 3.00 | 3.00 | 3.00 | 3.00 | 3.00 | 3.00 | 3.00 | 3.00 | 3.00 |
| | Cyclopentasiloxane | 4.00 | 4.00 | 4.00 | 4.00 | 4.00 | 4.00 | 4.00 | 4.00 | 4.00 |
| | Stearic Acid | 0.50 | 0.50 | 0.50 | 0.50 | 0.50 | 0.50 | 0.50 | 0.50 | 0.50 |
| | PEG-100 Stearate (and) Glyceryl Stearate | 0.80 | 0.80 | 0.80 | 0.80 | 0.80 | 0.80 | 0.80 | 0.80 | 0.80 |
| | Potassium Cetyl Phosphate | 1.30 | 1.30 | 1.30 | 1.30 | 1.30 | 1.30 | 1.30 | 1.30 | 1.30 |
| | VP/Eicosene Copolymer | 1.00 | 1.00 | 1.00 | 1.00 | 1.00 | 1.00 | 1.00 | 1.00 | 1.00 |
| | Ethylhexyl Methoxycinnamate | 7.00 | 7.00 | 7.00 | 7.00 | 7.00 | 7.00 | 7.00 | 7.00 | 7.00 |

-continued

| | O/W FORMULATION Anionic System emulsifier | | | | | | | | | |
|---|---|---|---|---|---|---|---|---|---|---|
| | Sun Milk INCI-Name | A % w/w | B % w/w | C % w/w | D % w/w | E % w/w | F % w/w | G % w/w | H % w/w | I % w/w |
| Part B | Octocrylene | 8.00 | 8.00 | 8.00 | 8.00 | 8.00 | 8.00 | 8.00 | 8.00 | 8.00 |
| | Diethylamino Hydroxy Benzoyl Hexyl Benzoate | | 4.00 | | | | | | | |
| | Zinc Oxide | | | 4.00 | | | | | | |
| | Ethylhexyl Salicylate | | | | | | | | 5.00 | |
| | Homosalate | | | | 10.00 | | | | | |
| | Methanone, 1,1'-(1,4-piperazinediyl)bis[1-[2-[4-(diethylamino)-2-hydroxybenzoyl]phenyl]- CAS number (919803-06-8) | 2.00 | 2.00 | 2.00 | 2.00 | 2.00 | 2.00 | 2.00 | 2.00 | 2.00 |
| | Methylene Bis-Benzotriazolyl Tetramethylbutylphenol * | | | | | 3.00 | | | | |
| | Titanium Dioxide *** | | | | | | 2.00 | | | |
| | Tris-Biphenyl Triazine * | | | | | | | 2.00 | | |
| | Phenylbenzimidazole Sulfonic Acid | | | | | | | | | 2.00 |
| | Aqua (Water) | Qs to 100 | Qs to 100 | Qs to 100 | Qs to 100 | Qs to 100 | Qs to 100 | Qs to 100 | Qs to 100 | Qs to 100 |
| | Propylene Glycol | 5.00 | 5.00 | 5.00 | 5.00 | 5.00 | 5.00 | 5.00 | 5.00 | 5.00 |
| | Xanthan Gum | 0.20 | 0.20 | 0.20 | 0.20 | 0.20 | 0.20 | 0.20 | 0.20 | 0.20 |
| | Acrylates/C10-30 Alkyl Acrylate Crosspolymer | 0.15 | 0.15 | 0.15 | 0.15 | 0.15 | 0.15 | 0.15 | 0.15 | 0.15 |
| | Disodium EDTA | 0.15 | 0.15 | 0.15 | 0.15 | 0.15 | 0.15 | 0.15 | 0.15 | 0.15 |
| Part C | Triethanolamine | Qs | Qs | Qs | Qs | Qs | Qs | Qs | Qs | Qs |
| | Dimethicone | 0.40 | 0.40 | 0.40 | 0.40 | 0.40 | 0.40 | 0.40 | 0.40 | 0.40 |
| | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.90 | 0.90 | 0.90 | 0.90 | 0.90 | 0.90 | 0.90 | 0.90 | 0.90 |
| | In vitro SPF measured according the method described | 21.90 | | | | | | | | |
| | UVA PF measured according the method described | 6.50 | | | | | | | | |

| | O/W FORMULATION Nonionic System emulsifier | | | | | | | | | |
|---|---|---|---|---|---|---|---|---|---|---|
| | Sun Cream INCI-Name | A % w/w | B % w/w | C % w/w | D % w/w | E % w/w | F % w/w | G % w/w | H % w/w | I % w/w |
| Part A | Tribehenin PEG-20 esters | 5.00 | 5.00 | 5.00 | 5.00 | 5.00 | 5.00 | 5.00 | 5.00 | 5.00 |
| | Phenethyl Benzoate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | Propylheptyl Caprylate | 1.00 | 1.00 | 1.00 | 1.00 | 1.00 | 1.00 | 1.00 | 1.00 | 1.00 |
| | Dibutyl Adipate | 2.00 | 2.00 | 2.00 | 2.00 | 2.00 | 2.00 | 2.00 | 2.00 | 2.00 |
| | PPG-2 Myristyl Ether Propionate | 2.00 | 2.00 | 2.00 | 2.00 | 2.00 | 2.00 | 2.00 | 2.00 | 2.00 |
| | Ethylhexyl Methoxycinnamate | 7.00 | 7.00 | 7.00 | 7.00 | 7.00 | 7.00 | 7.00 | 7.00 | 7.00 |
| | Bis-Ethylhexyloxyphenol Methoxyphenyl Triazine | 2.00 | 2.00 | 2.00 | 2.00 | 2.00 | 2.00 | 2.00 | 2.00 | 2.00 |
| | Diethylamino Hydroxy Benzoyl Hexyl Benzoate | | 4.00 | | | | | | | |
| | Ethylhexyl Salicylate | | | | | | | | 5.00 | |
| | Homosalate | | | | 10.00 | | | | | |
| Part B | Methanone, 1,1'-(1,4-piperazinediyl)bis[1-[2-[4-(diethylamino)-2-hydroxybenzoyl]phenyl]- CAS number (919803-06-8) | 2.00 | 2.00 | 2.00 | 2.00 | 2.00 | 2.00 | 2.00 | 2.00 | 2.00 |
| | Zinc Oxide | | | 4.00 | | | | | | |
| | Methylene Bis-Benzotriazolyl Tetramethylbutylphenol * | | | | | 3.00 | | | | |
| | Titanium Dioxide *** | | | | | | 2.00 | | | |
| | Tris-Biphenyl Triazine * | | | | | | | 2.00 | | |
| | Phenylbenzimidazole Sulfonic Acid | | | | | | | | | 2.00 |
| | Aqua (Water) | Qs to 100 | Qs to 100 | Qs to 100 | Qs to 100 | Qs to 100 | Qs to 100 | Qs to 100 | Qs to 100 | Qs to 100 |
| | VP/Dimethylaminoethylmethacrylate/Polycarbamyl Polyglycol Ester | 3.00 | 3.00 | 3.00 | 3.00 | 3.00 | 3.00 | 3.00 | 3.00 | 3.00 |
| | Disodium EDTA | 0.20 | 0.20 | 0.20 | 0.20 | 0.20 | 0.20 | 0.20 | 0.20 | 0.20 |
| | Sclerotium Gum | 2.00 | 2.00 | 2.00 | 2.00 | 2.00 | 2.00 | 2.00 | 2.00 | 2.00 |

-continued

O/W FORMULATION
Nonionic System emulsifier

| | Sun Cream INCI-Name | A % w/w | B % w/w | C % w/w | D % w/w | E % w/w | F % w/w | G % w/w | H % w/w | I % w/w |
|---|---|---|---|---|---|---|---|---|---|---|
| Part C | Ammonium Acryloyldimethyltaurate/Beheneth-25 Methacrylate Crosspolymer | 0.50 | 0.50 | 0.50 | 0.50 | 0.50 | 0.50 | 0.50 | 0.50 | 0.50 |
| | Cyclopentasiloxane (and) Cyclohexasiloxane | 4.00 | 4.00 | 4.00 | 4.00 | 4.00 | 4.00 | 4.00 | 4.00 | 4.00 |
| | Phenoxyethanol (and) Methylparaben (and) Ethylparaben (and) Butylparaben (and) Propylparaben (and) Isobutylparaben | 1.00 | 1.00 | 1.00 | 1.00 | 1.00 | 1.00 | 1.00 | 1.00 | 1.00 |
| | Sodium Hydroxide (and) Water | Qsp | Qsp | Qsp | Qsp | Qsp | Qsp | Qsp | Qsp | Qsp |
| | In vitro SPF measured according the method described | 19.00 | | | | | | | | |
| | UVA PF measured according the method described | 9.50 | | | | | | | | |

O/W FORMULATION
Gel

| Clear Sunscreen Gel INCI-Name | A % w/w | B % w/w | C % w/w | D % w/w | E % w/w | F % w/w | G % w/w | H % w/w | I % w/w |
|---|---|---|---|---|---|---|---|---|---|
| SD Alcohol 40 | Qs to 100 | Qs to 100 | Qs to 100 | Qs to 100 | Qs to 100 | Qs to 100 | Qs to 100 | Qs to 100 | Qs to 100 |
| Ethylhexyl Triazone | 2.00 | 2.00 | 2.00 | 2.00 | 2.00 | 2.00 | 2.00 | 2.00 | 2.00 |
| Methanone, 1,1'-(1,4-piperazineiyl)bis[1-[2-[4-(diethylamino)-2-hydroxybenzoyl]henyl]- CAS number (919803-06-8) | 2.00 | 2.00 | 2.00 | 2.00 | 2.00 | 2.00 | 2.00 | 2.00 | 2.00 |
| Diethylamino Hydroxy Benzoyl Hexyl Benzoate | | 4.00 | | | | | | | |
| Zinc Oxide | | | 4.00 | | | | | | |
| Methylene Bis-Benzotriazolyl Tetramethylbutylphenol * | | | | | 3.00 | | | | |
| Titanium Dioxide *** | | | | | | 2.00 | | | |
| Tris-Biphenyl Triazine * | | | | | | | 2.00 | | |
| Ethylhexyl Salicylate | | | | | | | | 5.00 | |
| Phenylbenzimidazole Sulfonic Acid | | | | | | | | | 2.00 |
| Homosalate | | | | 10.00 | | | | | |
| Phenethyl Benzoate | 4.00 | 4.00 | 4.00 | 4.00 | 4.00 | 4.00 | 4.00 | 4.00 | 4.00 |
| Tridecyl Trimellitate | 1.00 | 1.00 | 1.00 | 1.00 | 1.00 | 1.00 | 1.00 | 1.00 | 1.00 |
| Polyglyceryl-10 Eicosanedioate/Tetradecanedioate | 1.00 | 1.00 | 1.00 | 1.00 | 1.00 | 1.00 | 1.00 | 1.00 | 1.00 |
| Hydroxypropyl Cellulose | 1.70 | 1.70 | 1.70 | 1.70 | 1.70 | 1.70 | 1.70 | 1.70 | 1.70 |
| Isopropyl PPG-2 Isodeceth-7 Carboxylate | 9.70 | 9.70 | 9.70 | 9.70 | 9.70 | 9.70 | 9.70 | 9.70 | 9.70 |
| SD Alcohol 40 | 24.00 | 24.00 | 24.00 | 24.00 | 24.00 | 24.00 | 24.00 | 24.00 | 24.00 |
| Perfume | 0.60 | 0.60 | 0.60 | 0.60 | 0.60 | 0.60 | 0.60 | 0.60 | 0.60 |
| Aqua (Water) | 8.00 | 8.00 | 8.00 | 8.00 | 8.00 | 8.00 | 8.00 | 8.00 | 8.00 |
| In vitro SPF measured according the method described | 7.50 | | | | | | | | |
| UVA PF measured according the method described | 3.50 | | | | | | | | |

| Gel Cream INCI-Name | A % w/w | B % w/w | C % w/w | D % w/w | E % w/w | F % w/w | G % w/w | H % w/w | I % w/w |
|---|---|---|---|---|---|---|---|---|---|
| Acrylates/C10-30 Alkyl Acrylate Crosspolymer | 0.40 | 0.40 | 0.40 | 0.40 | 0.40 | 0.40 | 0.40 | 0.40 | 0.40 |
| Polyacrylic Acid | 0.20 | 0.20 | 0.20 | 0.20 | 0.20 | 0.20 | 0.20 | 0.20 | 0.20 |
| Phenethyl Benzoate | 2.00 | 2.00 | 2.00 | 2.00 | 2.00 | 2.00 | 2.00 | 2.00 | 2.00 |
| Diisopropyl Sebacate | 0.50 | 0.50 | 0.50 | 0.50 | 0.50 | 0.50 | 0.50 | 0.50 | 0.50 |
| Xanthan Gum | 0.10 | 0.10 | 0.10 | 0.10 | 0.10 | 0.10 | 0.10 | 0.10 | 0.10 |
| Cetearyl alcohol | 3.00 | 3.00 | 3.00 | 3.00 | 3.00 | 3.00 | 3.00 | 3.00 | 3.00 |
| C12-15 Alkyl Benzoate | 2.00 | 2.00 | 2.00 | 2.00 | 2.00 | 2.00 | 2.00 | 2.00 | 2.00 |
| Caprylic/Capric Triglyceride | 1.00 | 1.00 | 1.00 | 1.00 | 1.00 | 1.00 | 1.00 | 1.00 | 1.00 |
| Dimethicone | 5.00 | 5.00 | 5.00 | 5.00 | 5.00 | 5.00 | 5.00 | 5.00 | 5.00 |
| Dimethiconol | 1.00 | 1.00 | 1.00 | 1.00 | 1.00 | 1.00 | 1.00 | 1.00 | 1.00 |
| Diethylhexyl Butamido Triazone | 1.00 | 1.00 | 1.00 | 1.00 | 1.00 | 1.00 | 1.00 | 1.00 | 1.00 |

-continued

| Gel Cream INCI-Name | A % w/w | B % w/w | C % w/w | D % w/w | E % w/w | F % w/w | G % w/w | H % w/w | I % w/w |
|---|---|---|---|---|---|---|---|---|---|
| Methanone, 1,1'-(1,4-piperazineiyl)bis[1-[2-[4-(diethylamino)-2-hydroxybenzoyl]phenyl]- CAS number (919803-06-8) | 2.00 | 2.00 | 2.00 | 2.00 | 2.00 | 2.00 | 2.00 | 2.00 | 2.00 |
| Diethylamino Hydroxy Benzoyl Hexyl Benzoate | | 4.00 | | | | | | | |
| Zinc Oxide | | | 4.00 | | | | | | |
| Methylene Bis-Benzotriazolyl Tetramethylbutylphenol * | | | | | 3.00 | | | | |
| Titanium Dioxide *** | | | | | | 2.00 | | | |
| Tris-Biphenyl Triazine * | | | | | | | 2.00 | | |
| Ethylhexyl Salicylate | | | | | | | | 5.00 | |
| Phenylbenzimidazole Sulfonic Acid | | | | | | | | | 2.00 |
| Homosalate | | | | 10.00 | | | | | |
| Glycerin | 3.00 | 3.00 | 3.00 | 3.00 | 3.00 | 3.00 | 3.00 | 3.00 | 3.00 |
| Sodium Hydroxide | q.s. | q.s. | q.s. | q.s. | q.s. | q.s. | q.s. | q.s. | q.s. |
| Preservatives | .q.s. | .q.s. | .q.s. | .q.s. | .q.s. | .q.s. | .q.s. | .q.s. | .q.s. |
| Perfume | q.s. | q.s. | q.s. | q.s. | q.s. | q.s. | q.s. | q.s. | q.s. |
| Aqua (Water) | ad 100.0 | ad 100.0 | ad 100.0 | ad 100.0 | ad 100.0 | ad 100.0 | ad 100.0 | ad 100.0 | ad 100.0 |
| PH-value adjusted to 6.0 | | | | | | | | | |
| In vitro SPF measured according the method described | 5.00 | | | | | | | | |
| UVA PF measured according the method described | 3.50 | | | | | | | | |

| O/W FORMULATION Emulsifier Free | | | | | | | | | |
|---|---|---|---|---|---|---|---|---|---|
| INCI-Name | A % w/w | B % w/w | C % w/w | D % w/w | E % w/w | F % w/w | G % w/w | H % w/w | I % w/w |
| Sodium Carbomer | 0.20 | 0.20 | 0.20 | 0.20 | 0.20 | 0.20 | 0.20 | 0.20 | 0.20 |
| Xanthan Gum | 0.30 | 0.30 | 0.30 | 0.30 | 0.30 | 0.30 | 0.30 | 0.30 | 0.30 |
| Butyl Methoxydibenzoylmethane | 3.00 | 3.00 | 3.00 | 3.00 | 3.00 | 3.00 | 3.00 | 3.00 | 3.00 |
| Methanone, 1,1'-(1,4-piperaineiyl)bis[1-[2-[4-(diethylamino)-2-hydroxybenzoyl]phenyl]- CAS number (919803-06-8) | 2.00 | 2.00 | 2.00 | 2.00 | 2.00 | 2.00 | 2.00 | 2.00 | 2.00 |
| Diethylamino Hydroxy Benzoyl Hexyl Benzoate | | 4.00 | | | | | | | |
| Methylene Bis-Benzotriazolyl Tetramethylbutylphenol * | | | | | 3.00 | | | | |
| Titanium Dioxide *** | | | | | | 2.00 | | | |
| Tris-Biphenyl Triazine * | | | | | | | 2.00 | | |
| Ethylhexyl Salicylate | | | | | | | | 5.00 | |
| Phenylbenzimidazole Sulfonic Acid | | | | | | | | | 2.00 |
| Homosalate | | | | 10.00 | | | | | |
| Bis-Ethylhexyloxyphenol Methoxyphenyl Triazine ** | | 2.00 | | | | | | | |
| Phenethyl Benzoate | 4.00 | 4.00 | 4.00 | 4.00 | 4.00 | 4.00 | 4.00 | 4.00 | 4.00 |
| Tridecyl Trimellitate | 2.00 | 2.00 | 2.00 | 2.00 | 2.00 | 2.00 | 2.00 | 2.00 | 2.00 |
| Isodecyl Salicylate | 1.00 | 1.00 | 1.00 | 1.00 | 1.00 | 1.00 | 1.00 | 1.00 | 1.00 |
| C12-15 Alkyl Benzoate | 1.00 | 1.00 | 1.00 | 1.00 | 1.00 | 1.00 | 1.00 | 1.00 | 1.00 |
| Dicaprylyl Carbonate | 1.00 | 1.00 | 1.00 | 1.00 | 1.00 | 1.00 | 1.00 | 1.00 | 1.00 |
| Dimethicone | 0.50 | 0.50 | 0.50 | 0.50 | 0.50 | 0.50 | 0.50 | 0.50 | 0.50 |
| Butyrospermum Parkii (Shea) Butter | 2.00 | 2.00 | 2.00 | 2.00 | 2.00 | 2.00 | 2.00 | 2.00 | 2.00 |
| Ethylhexylglycerin | 0.50 | 0.50 | 0.50 | 0.50 | 0.50 | 0.50 | 0.50 | 0.50 | 0.50 |
| Glycerin | 7.50 | 7.50 | 7.50 | 7.50 | 7.50 | 7.50 | 7.50 | 7.50 | 7.50 |
| Glycine Soja (Soybean) Extract | 1.50 | 1.50 | 1.50 | 1.50 | 1.50 | 1.50 | 1.50 | 1.50 | 1.50 |
| Vitamin E Acetate | 0.20 | 0.20 | 0.20 | 0.20 | 0.20 | 0.20 | 0.20 | 0.20 | 0.20 |
| Glucosylrutin | 0.30 | 0.30 | 0.30 | 0.30 | 0.30 | 0.30 | 0.30 | 0.30 | 0.30 |
| Polyethylene Terephthalate | 0.50 | 0.50 | 0.50 | 0.50 | 0.50 | 0.50 | 0.50 | 0.50 | 0.50 |
| Trisodium EDTA | 0.30 | 0.30 | 0.30 | 0.30 | 0.30 | 0.30 | 0.30 | 0.30 | 0.30 |
| Alcohol | 7.00 | 7.00 | 7.00 | 7.00 | 7.00 | 7.00 | 7.00 | 7.00 | 7.00 |
| Aqua (Water) | ad 100 | ad 100 | ad 100 | ad 100 | ad 100 | ad 100 | ad 100 | ad 100 | ad 100 |
| In vitro SPF measured according the method described | 3.80 | | | | | | | | |
| UVA PF measured according the method described | 6.50 | | | | | | | | |

SPRAY FORMULATION
Classic

| | Sun spray<br>INCI-Name | A<br>% w/w | B<br>% w/w | C<br>% w/w | D<br>% w/w | E<br>% w/w | F<br>% w/w | G<br>% w/w | H<br>% w/w | I<br>% w/w |
|---|---|---|---|---|---|---|---|---|---|---|
| Part A | Cyclopentasiloxane | 2.50 | 2.50 | 2.50 | 2.50 | 2.50 | 2.50 | 2.50 | 2.50 | 2.50 |
| | Hydrogenated Coco-Glycerides | 1.50 | 1.50 | 1.50 | 1.50 | 1.50 | 1.50 | 1.50 | 1.50 | 1.50 |
| | Phenethyl Benzoate | 4.00 | 4.00 | 4.00 | 4.00 | 4.00 | 4.00 | 4.00 | 4.00 | 4.00 |
| | Triisodecyl Trimellitate | 2.00 | 2.00 | 2.00 | 2.00 | 2.00 | 2.00 | 2.00 | 2.00 | 2.00 |
| | Triheptanoin | 1.00 | 1.00 | 1.00 | 1.00 | 1.00 | 1.00 | 1.00 | 1.00 | 1.00 |
| | C12-15 Alkyl Benzoate | 3.60 | 3.60 | 3.60 | 3.60 | 3.60 | 3.60 | 3.60 | 3.60 | 3.60 |
| | Ethylhexyl Methoxycinnamate | 7.00 | 7.00 | 7.00 | 7.00 | 7.00 | 7.00 | 7.00 | 7.00 | 7.00 |
| | Octocrylene | 8.00 | 8.00 | 8.00 | 8.00 | 8.00 | 8.00 | 8.00 | 8.00 | 8.00 |
| | Diethylamino Hydroxy Benzoyl Hexyl Benzoate | | 4.00 | | | | | | | |
| | Ethylhexyl Salicylate | | | | | | | | 5.00 | |
| | Homosalate | | | | 10.00 | | | | | |
| | Merocyanine of formula (A) or (B) | | | | | | | | | |
| Part B | Methanone, 1,1'-(1,4-piperazine-iyl)bis[1-[2-[4-(diethylamino)-2-hydroxybenzoyl]phenyl]- CAS number (919803-06-8) | 4.00 | 4.00 | 4.00 | 4.00 | 4.00 | 4.00 | 4.00 | 4.00 | 4.00 |
| | Methylene Bis-Benzotriazolyl Tetramethylbutylphenol * | | | | | 3.00 | | | | |
| | Titanium Dioxide *** | | | | | | 2.00 | | | |
| | Tris-Biphenyl Triazine * | | | | | | | 2.00 | | |
| | Phenylbenzimidazole Sulfonic Acid | | | | | | | | | 2.00 |
| | Water (and) Caprylic/Capric Tri-glyceride (and) Glycerin (and) Ceteareth-25 (and) Disodium Ethylene Dicocamide PEG-15 Disulfate (and) Sodium Lauroyl Lactylate (and) Behenyl Alcohol (and) Glyceryl Stearate (and) Glyceryl Stearate Citrate (and) Xanthan Gum | 10.00 | 10.00 | 10.00 | 10.00 | 10.00 | 10.00 | 10.00 | 10.00 | 10.00 |
| | VP/Hexadecene Copolymer | 0.50 | 0.50 | 0.50 | 0.50 | 0.50 | 0.50 | 0.50 | 0.50 | 0.50 |
| | Glycerin | 3.00 | 3.00 | 3.00 | 3.00 | 3.00 | 3.00 | 3.00 | 3.00 | 3.00 |
| | Aqua (Water) | Qs to 100 | Qs to 100 | Qs to 100 | Qs to 100 | Qs to 100 | Qs to 100 | Qs to 100 | Qs to 100 | Qs to 100 |
| Part C | Alcohol Denat. | 7.00 | 7.00 | 7.00 | 7.00 | 7.00 | 7.00 | 7.00 | 7.00 | 7.00 |
| Part D | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.60 | 0.60 | 0.60 | 0.60 | 0.60 | 0.60 | 0.60 | 0.60 | 0.60 |
| | In vitro SPF measured according the method described | 25.80 | | | | | | | | |
| | UVA PF measured according the method described | 9.00 | | | | | | | | |

SPRAY FORMULATION
Foaming

| Foamable O/W Lotion<br>INCI-Name | A<br>% w/w | B<br>% w/w | C<br>% w/w | D<br>% w/w | E<br>% w/w | F<br>% w/w | G<br>% w/w | H<br>% w/w | I<br>% w/w |
|---|---|---|---|---|---|---|---|---|---|
| Stearic Acid | 3.00 | 3.00 | 3.00 | 3.00 | 3.00 | 3.00 | 3.00 | 3.00 | 3.00 |
| Cetearyl Alcohol | 2.00 | 2.00 | 2.00 | 2.00 | 2.00 | 2.00 | 2.00 | 2.00 | 2.00 |
| PEG-100 Stearate | 2.00 | 2.00 | 2.00 | 2.00 | 2.00 | 2.00 | 2.00 | 2.00 | 2.00 |
| Mineral Oil | 3.00 | 3.00 | 3.00 | 3.00 | 3.00 | 3.00 | 3.00 | 3.00 | 3.00 |
| Dimethicone | 1.00 | 1.00 | 1.00 | 1.00 | 1.00 | 1.00 | 1.00 | 1.00 | 1.00 |
| Cyclomethicone | 2.00 | 2.00 | 2.00 | 2.00 | 2.00 | 2.00 | 2.00 | 2.00 | 2.00 |
| Ethylhexyl Triazone | 2.00 | 2.00 | 2.00 | 2.00 | 2.00 | 2.00 | 2.00 | 2.00 | 2.00 |
| Methanone, 1,1'-(1,4-piperazine-diyl)bis[1-[2-[4-(diethylamino)-2-hydroxybenzoyl]phenyl]- CAS number (919803-06-8) | 4.00 | 4.00 | 4.00 | 4.00 | 4.00 | 4.00 | 4.00 | 4.00 | 4.00 |
| Diethylamino Hydroxy Benzoyl Hexyl Benzoate | | 4.00 | | | | | | | |
| Methylene Bis-Benzotriazolyl Tetramethylbutylphenol * | | | | | 3.00 | | | | |
| Titanium Dioxide *** | | | | | | 2.00 | | | |
| Tris-Biphenyl Triazine * | | | | | | | 2.00 | | |
| Ethylhexyl Salicylate | | | | | | | | 5.00 | |
| Phenylbenzimidazole Sulfonic | | | | | | | | | 2.00 |

-continued

| SPRAY FORMULATION Foaming | | | | | | | | | |
|---|---|---|---|---|---|---|---|---|---|
| Foamable O/W Lotion INCI-Name | A % w/w | B % w/w | C % w/w | D % w/w | E % w/w | F % w/w | G % w/w | H % w/w | I % w/w |
| Acid | | | | | | | | | |
| Homosalate | | | | 10.00 | | | | | |
| Merocyanine of formula (A) or (B) | | | | | | | | | |
| Vitamin E Acetate | 2.00 | 2.00 | 2.00 | 2.00 | 2.00 | 2.00 | 2.00 | 2.00 | 2.00 |
| Petrolatum | 2.50 | 2.50 | 2.50 | 2.50 | 2.50 | 2.50 | 2.50 | 2.50 | 2.50 |
| Glycerin | 3.50 | 3.50 | 3.50 | 3.50 | 3.50 | 3.50 | 3.50 | 3.50 | 3.50 |
| Cellulose Gum | 0.05 | 0.05 | 0.05 | 0.05 | 0.05 | 0.05 | 0.05 | 0.05 | 0.05 |
| Magnesium Aluminium Silicate | 0.50 | 0.50 | 0.50 | 0.50 | 0.50 | 0.50 | 0.50 | 0.50 | 0.50 |
| Kaolin | 0.05 | 0.05 | 0.05 | 0.05 | 0.05 | 0.05 | 0.05 | 0.05 | 0.05 |
| Talc | 0.50 | 0.50 | 0.50 | 0.50 | 0.50 | 0.50 | 0.50 | 0.50 | 0.50 |
| Perfume | q.s. | q.s. | q.s. | q.s. | q.s. | q.s. | q.s. | q.s. | q.s. |
| Preservatives | q.s. | q.s. | q.s. | q.s. | q.s. | q.s. | q.s. | q.s. | q.s. |
| Colorants/Dyes/Pigments/Pearls | q.s. | q.s. | q.s. | q.s. | q.s. | q.s. | q.s. | q.s. | q.s. |
| Sodium Hydroxide | q.s. | q.s. | q.s. | q.s. | q.s. | q.s. | q.s. | q.s. | q.s. |
| Aqua (Water) | ad 100.00 | ad 100.00 | ad 100.00 | ad 100.00 | ad 100.00 | ad 100.00 | ad 100.00 | ad 100.00 | ad 100.00 |
| pH-value adjusted to 6.0-7. | | | | | | | | | |
| Pentane | Qs | Qs | Qs | Qs | Qs | Qs | Qs | Qs | Qs |
| In vitro SPF measured according the method described | 8.70 | | | | | | | | |
| UVA PF measured according the method described | 5.40 | | | | | | | | |

| SPRAY FORMULATION Continuous | | | | | | | | | |
|---|---|---|---|---|---|---|---|---|---|
| Continuous Spray kids INCI-Name | A % w/w | B % w/w | C % w/w | D % w/w | E % w/w | F % w/w | G % w/w | H % w/w | I % w/w |
| C12-15 Alkyl Benzoate | 5.00 | 5.00 | 5.00 | 5.00 | 5.00 | 5.00 | 5.00 | 5.00 | 5.00 |
| Acrylates/C12-22 Alkyl Methacrylate Copolymer | 3.00 | 3.00 | 3.00 | 3.00 | 3.00 | 3.00 | 3.00 | 3.00 | 3.00 |
| Octyldodecyl Neopentanoate | 3.00 | 3.00 | 3.00 | 3.00 | 3.00 | 3.00 | 3.00 | 3.00 | 3.00 |
| Glycerin | 2.00 | 2.00 | 2.00 | 2.00 | 2.00 | 2.00 | 2.00 | 2.00 | 2.00 |
| Ceteareth-20 | 1.00 | 1.00 | 1.00 | 1.00 | 1.00 | 1.00 | 1.00 | 1.00 | 1.00 |
| Caprylyl Glycol | 1.00 | 1.00 | 1.00 | 1.00 | 1.00 | 1.00 | 1.00 | 1.00 | 1.00 |
| *Aloe Barbadensis* Leaf Extract | 1.00 | 1.00 | 1.00 | 1.00 | 1.00 | 1.00 | 1.00 | 1.00 | 1.00 |
| Tocopheryl Acetate | 0.70 | 0.70 | 0.70 | 0.70 | 0.70 | 0.70 | 0.70 | 0.70 | 0.70 |
| Diethylhexyl Butamido Triazone | 1.00 | 1.00 | 1.00 | 1.00 | 1.00 | 1.00 | 1.00 | 1.00 | 1.00 |
| Methanone, 1,1'-(1,4-piperazinediyl)bis[1-[2-[4-(diethylamino)-2-hydroxybenzoyl]phenyl]- CAS number (919803-06-8) | 4.00 | 4.00 | 4.00 | 4.00 | 4.00 | 4.00 | 4.00 | 4.00 | 4.00 |
| Diethylamino Hydroxy Benzoyl Hexyl Benzoate | | 4.00 | | | | | | | |
| Polysilicone-15 | | | 5.00 | | | | | | |
| Methylene Bis-Benzotriazolyl Tetramethylbutylphenol * | | | | | 3.00 | | | | |
| Titanium Dioxide *** | | | | | | 2.00 | | | |
| Tris-Biphenyl Triazine * | | | | | | | 2.00 | | |
| Ethylhexyl Salicylate | | | | | | | | 5.00 | |
| Phenylbenzimidazole Sulfonic Acid | | | | | | | | | 2.00 |
| Homosalate | | | | 10.00 | | | | | |
| Microcrystalline Cellulose (and) Cellulose Gum | 0.30 | 0.30 | 0.30 | 0.30 | 0.30 | 0.30 | 0.30 | 0.30 | 0.30 |
| Disodium Ethylene Dicocamide PEG-15 Disulfate (and) Sodium Lauroyl Lactylate | 2.00 | 2.00 | 2.00 | 2.00 | 2.00 | 2.00 | 2.00 | 2.00 | 2.00 |
| Behenyl Alcohol (and) Glyceryl Stearate (and) Glyceryl Stearate Citrate (and) Disodium Ethylene Dicocamide PEG-15 Disulfate | 0.50 | 0.50 | 0.50 | 0.50 | 0.50 | 0.50 | 0.50 | 0.50 | 0.50 |
| *Acacia Senegal* Gum | 0.20 | 0.20 | 0.20 | 0.20 | 0.20 | 0.20 | 0.20 | 0.20 | 0.20 |
| Triethanolamine | 0.15 | 0.15 | 0.15 | 0.15 | 0.15 | 0.15 | 0.15 | 0.15 | 0.15 |
| Methyldibromo Glutaronitrile (and) Methylchloroisothiazolinone (and) Methylisothiazolinone (and) Phenoxyethanol | 0.5 | 0.5 | 0.5 | 0.5 | 0.5 | 0.5 | 0.5 | 0.5 | 0.5 |

-continued

| SPRAY FORMULATION Continuous | | | | | | | | | |
|---|---|---|---|---|---|---|---|---|---|
| Continuous Spray kids INCI-Name | A % w/w | B % w/w | C % w/w | D % w/w | E % w/w | F % w/w | G % w/w | H % w/w | I % w/w |
| Acrylates/C10-30 Alkyl Acrylate Crosspolymer | 0.15 | 0.15 | 0.15 | 0.15 | 0.15 | 0.15 | 0.15 | 0.15 | 0.15 |
| Disodium EDTA | 0.10 | 0.10 | 0.10 | 0.10 | 0.10 | 0.10 | 0.10 | 0.10 | 0.10 |
| BHT | 0.05 | 0.05 | 0.05 | 0.05 | 0.05 | 0.05 | 0.05 | 0.05 | 0.05 |
| Perfume | q.s. | q.s. | q.s. | q.s. | q.s. | q.s. | q.s. | q.s. | q.s. |
| Aqua (Water) | ad 100.00 | ad 100.00 | ad 100.00 | ad 100.00 | ad 100.00 | ad 100.00 | ad 100.00 | ad 100.00 | ad 100.00 |
| Isobutane | Qs | Qs | Qs | Qs | Qs | Qs | Qs | Qs | Qs |
| In vitro SPF measured according the method described | 5.80 | | | | | | | | |
| UVA PF measured according the method described | 5.40 | | | | | | | | |

| | | SPRAY FORMULATION Clear | | | | | | | | |
|---|---|---|---|---|---|---|---|---|---|---|
| | Clear alcohol spray INCI-Name | A % w/w | B % w/w | C % w/w | D % w/w | E % w/w | F % w/w | G % w/w | H % w/w | I % w/w |
| Part A | Diethylhexyl Carbonate | 15.00 | 15.00 | 15.00 | 15.00 | 15.00 | 15.00 | 15.00 | 15.00 | 15.00 |
| | Hexyl Laurate | 8.00 | 8.00 | 8.00 | 8.00 | 8.00 | 8.00 | 8.00 | 8.00 | 8.00 |
| | Dicaprylyl Carbonate | 5.00 | 5.00 | 5.00 | 5.00 | 5.00 | 5.00 | 5.00 | 5.00 | 5.00 |
| | Diethylamino Hydroxy Benzoyl Hexyl Benzoate | | 4.00 | | | | | | | |
| | Polysilicone-15 | | | 5.00 | | | | | | |
| | Titanium Dioxide *** | | | | | | | 2.00 | | |
| | Ethylhexyl Salicylate | | | | | | | | 5.00 | |
| | Disodium Phenyl Dibenzylmidazole Tetrasulfonate | | | | | 2.00 | | | | |
| | Ethylhexyl Methoxycinnamate | 7.00 | 7.00 | 7.00 | 7.00 | 7.00 | 7.00 | 7.00 | 7.00 | 7.00 |
| | Bis-Ethylhexyloxyphenol Methoxyphenyl Triazine | 3.00 | 3.00 | 3.00 | 3.00 | 3.00 | 3.00 | 3.00 | 3.00 | 3.00 |
| Part B | Alcohol | Qs. 100 | Qs. 100 | Qs. 100 | Qs. 100 | Qs. 100 | Qs. 100 | Qs. 100 | Qs. 100 | Qs. 100 |
| | Methylene Bis-Benzotriazolyl Tetramethylbutylphenol * | | | | | | 3.00 | | | |
| | Tris-Biphenyl Triazine * | | | | | | | | 2.00 | |
| | Phenylbenzimidazole Sulfonic Acid | | | | | | | | | 2.00 |
| | Methanone, 1,1'-(1,4-piperainediyl)bis[1-[2-[4-(diethylamino)-2-hydroxybenzoyl]phenyl]- CAS number (919803-06-8) | 2.00 | 2.00 | 2.00 | 2.00 | 2.00 | 2.00 | 2.00 | 2.00 | 2.00 |
| Part C | Cyclopentasiloxane (and) Cyclohexasiloxane | 15.00 | 15.00 | 15.00 | 15.00 | 15.00 | 15.00 | 15.00 | 15.00 | 15.00 |

Manufacturing Instruction:
Heat part A at 75° C. until homogeneous, then cool down to room temperature. Mix part C with part B under stirrer.
Then add part A to part B + C under stirrer and mix until homogeneous.

| | |
|---|---|
| In vitro SPF measured according the method described | 22.80 |
| UVA PF measured according the method described | 11.50 |

| | | W/O FORMULATION | | | | | | | | |
|---|---|---|---|---|---|---|---|---|---|---|
| | Soft Sense Shake Well INCI-Name | A % w/w | B % w/w | C % w/w | D % w/w | E % w/w | F % w/w | G % w/w | H % w/w | I % w/w |
| Part A | Tetradibutyl Pentaerithrityl Hydroxyhydrocinnamate | 0.02 | 0.02 | 0.02 | 0.02 | 0.02 | 0.02 | 0.02 | 0.02 | 0.02 |
| | Ethylhexyl Methoxycinnamate | 8.00 | 8.00 | 8.00 | 8.00 | 8.00 | 8.00 | 8.00 | 8.00 | 8.00 |
| | Bis-Ethylhexyloxyphenol Methoxyphenyl Triazine | 3.00 | 3.00 | 3.00 | 3.00 | 3.00 | 3.00 | 3.00 | 3.00 | 3.00 |
| | Diethylamino Hydroxy Benzoyl Hexyl Benzoate | | 4.00 | | | | | | | |
| | Polysilicone-15 | | | 5.00 | | | | | | |
| | Ethylhexyl Salicylate | | | | | | | | 5.00 | |
| | Benzophenone-3 | | | | 3.00 | | | | | |
| | Ethylhexyl Benzoate | 10.00 | 10.00 | 10.00 | 10.00 | 10.00 | 10.00 | 10.00 | 10.00 | 10.00 |

| W/O FORMULATION | | | | | | | | | | |
|---|---|---|---|---|---|---|---|---|---|---|
| | Soft Sense Shake Well INCI-Name | A % w/w | B % w/w | C % w/w | D % w/w | E % w/w | F % w/w | G % w/w | H % w/w | I % w/w |
| | Dicaprylyl Carbonate | 2.00 | 2.00 | 2.00 | 2.00 | 2.00 | 2.00 | 2.00 | 2.00 | 2.00 |
| Part B | Cyclopentasiloxane | 11.00 | 11.00 | 11.00 | 11.00 | 11.00 | 11.00 | 11.00 | 11.00 | 11.00 |
| | Ethyl Trisiloxane | 11.00 | 11.00 | 11.00 | 11.00 | 11.00 | 11.00 | 11.00 | 11.00 | 11.00 |
| | Caprylyl Trimethicone | 1.00 | 1.00 | 1.00 | 1.00 | 1.00 | 1.00 | 1.00 | 1.00 | 1.00 |
| | Dimethicone (and) Isododecane | 1.00 | 1.00 | 1.00 | 1.00 | 1.00 | 1.00 | 1.00 | 1.00 | 1.00 |
| Part C | Vinyl Dimethione/Methione Silsesquioxane Crosspoymer | 2.00 | 2.00 | 2.00 | 2.00 | 2.00 | 2.00 | 2.00 | 2.00 | 2.00 |
| | Polyglyceryl-3 Polydmehyl-iloxyethyl Dimethicone | 3.00 | 3.00 | 3.00 | 3.00 | 3.00 | 3.00 | 3.00 | 3.00 | 3.00 |
| Part D | Aqua (Water) | Qs to 100 | Qs to 100 | Qs to 100 | Qs to 100 | Qs to 100 | Qs to 100 | Qs to 100 | Qs to 100 | Qs to 100 |
| | Methylene Bis-Benzotriazolyl Tetramethylbutylphenol * | | | | | 3.00 | | | | |
| | Titanium Dioxide *** | | | | | | 2.00 | | | |
| | Tris-Biphenyl Triazine * | | | | | | | 2.00 | | |
| | Phenylbenzimidazole Sulfonic Acid | | | | | | | | | 2.00 |
| | Butylene Glycol | 2.00 | 2.00 | 2.00 | 2.00 | 2.00 | 2.00 | 2.00 | 2.00 | 2.00 |
| | Magnesium Sulfate | 1.00 | 1.00 | 1.00 | 1.00 | 1.00 | 1.00 | 1.00 | 1.00 | 1.00 |
| | Aqua (and) Tocopheryl Acetate (and) Capryic/Capric Triglyceride (and) Polysorbate 80 (and) Lecithin | 3.00 | 3.00 | 3.00 | 3.00 | 3.00 | 3.00 | 3.00 | 3.00 | 3.00 |
| | Disodium EDTA | 0.20 | 0.20 | 0.20 | 0.20 | 0.20 | 0.20 | 0.20 | 0.20 | 0.20 |
| | Methanone, 1,1'-(1,4-piperazinediyl)bis[1-[2-[4-(diethylamino)-2-hydroxy-enzoyl]phenyl]- CAS number (919803-06-8) | 3.00 | 3.00 | 3.00 | 3.00 | 3.00 | 3.00 | 3.00 | 3.00 | 3.00 |
| Part E | Alcohol | 7.00 | 7.00 | 7.00 | 7.00 | 7.00 | 7.00 | 7.00 | 7.00 | 7.00 |
| | Aluminum Starch Octenylsuccinate | 2.00 | 2.00 | 2.00 | 2.00 | 2.00 | 2.00 | 2.00 | 2.00 | 2.00 |
| | Preservatives | Qs | Qs | Qs | Qs | Qs | Qs | Qs | Qs | Qs |

Manufacturing Instruction:
Heat up part A to 80° C. Cool down to room temperature. Add the ingredients of part B into part A and homogenize with an Ultra Turrax. Mix part C. Slowly add part C into A + B under increased stirring speed. Then add the ingredients of part D and homogenize shortly. Continue stirring to room temperature.

|   |   |
|---|---|
| In vitro SPF measured according the method described | 26.70 |
| UVA PF measured according the method described | 13.80 |

| W/Si FORMULATION | | | | | | | | | | |
|---|---|---|---|---|---|---|---|---|---|---|
| | Shake Well Sunscreen, Shake before use NCI-Name | A % w/w | B % w/w | C % w/w | D % w/w | E % w/w | F % w/w | G % w/w | H % w/w | I % w/w |
| Part A | Cyclopentasiloxane (and) C6-8 Alkyl C3-6 Alkyl Glucoside Dimethicone (and) Trimethylsiloxysilicate | 8.00 | 8.00 | 8.00 | 8.00 | 8.00 | 8.00 | 8.00 | 8.00 | 8.00 |
| | Polyglyceryl-6 Polyricinoleate | 1.00 | 1.00 | 1.00 | 1.00 | 1.00 | 1.00 | 1.00 | 1.00 | 1.00 |
| | Cetyl PEG/PPG-10/1 Dimethicone | 0.33 | 0.33 | 0.33 | 0.33 | 0.33 | 0.33 | 0.33 | 0.33 | 0.33 |
| | Cyclopentasiloxane | 11.00 | 11.00 | 11.00 | 11.00 | 11.00 | 11.00 | 11.00 | 11.00 | 11.00 |
| | Isopropyl Palmitate | 5.00 | 5.00 | 5.00 | 5.00 | 5.00 | 5.00 | 5.00 | 5.00 | 5.00 |
| | Squalane | 5.00 | 5.00 | 5.00 | 5.00 | 5.00 | 5.00 | 5.00 | 5.00 | 5.00 |
| | Dimethicone | 5.00 | 5.00 | 5.00 | 5.00 | 5.00 | 5.00 | 5.00 | 5.00 | 5.00 |
| | Butyl Methoxydibenzoylmethane | 5.00 | 5.00 | 5.00 | 5.00 | 5.00 | 5.00 | 5.00 | 5.00 | 5.00 |
| | Diethylamino Hydroxy Benzoyl Hexyl Benzoate | | 4.00 | | | | | | | |
| | Isoamyl p-Methoxycinnamate | | | 3.00 | | | | | | |
| | Ethylhexyl Salicylate | | | | | | | | 5.00 | |
| | Benzophenone-3 | | | | 3.00 | | | | | |
| Part B | Aqua (Water) | qs to 100 | qs to 100 | qs to 100 | qs to 100 | qs to 100 | qs to 100 | qs to 100 | qs to 100 | qs to 100 |
| | Methanone, 1,1'-(1,4-piperazinediyl)bis[1-[2-[4-(diethylamino)-2-hydroxybenzoyl]-phenyl]- CAS number (919803-06-8) | 1.00 | 1.00 | 1.00 | 1.00 | 1.00 | 1.00 | 1.00 | 1.00 | 1.00 |
| | Methylene Bis-Benzotriazolyl Tetramethylbutylphenol * | | | | | 3.00 | | | | |

W/Si FORMULATION

| Shake Well Sunscreen, Shake before use NCI-Name | A % w/w | B % w/w | C % w/w | D % w/w | E % w/w | F % w/w | G % w/w | H % w/w | I % w/w |
|---|---|---|---|---|---|---|---|---|---|
| Titanium Dioxide *** | | | | | | 2.00 | | | |
| Tris-Biphenyl Triazine * | | | | | | | 2.00 | | |
| Terephthalylidene Dicamphor Sulfonic Acid | | | | | | | | | 2.00 |
| Magnesium Sulfate | 0.50 | 0.50 | 0.50 | 0.50 | 0.50 | 0.50 | 0.50 | 0.50 | 0.50 |
| Preservatives | qs | qs | qs | qs | qs | qs | qs | qs | qs |

Manufacturing Instruction:
Mix part A and part B separately. Pour part B into part A under increased stirring speed. Let stir for a short moment.

| | | |
|---|---|---|
| In vitro SPF measured according the method described | | 4.50 |
| UVA PF measured according the method described | | 5.50 |

Lipstick FORMULATION

| | Ultrashine Lip Kiss- Mauve Tendance INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | *Euphorbia Cerifera* (Candelilla) Wax | 8.50 | 8.50 | 8.50 | 8.50 | 8.50 | 8.50 | 8.50 | 8.50 | 8.50 |
| | Synthetic Wax | 8.00 | 8.00 | 8.00 | 8.00 | 8.00 | 8.00 | 8.00 | 8.00 | 8.00 |
| | Bis-Behenyl/Isostearyl/Phytosteryl Dimer Dilinoleyl Dimer Dilinoleate | 7.00 | 7.00 | 7.00 | 7.00 | 7.00 | 7.00 | 7.00 | 7.00 | 7.00 |
| Part B | Tridecyl Trimellilate | 25.00 | 25.00 | 25.00 | 25.00 | 25.00 | 25.00 | 25.00 | 25.00 | 25.00 |
| | Ethylhexyl Methoxycinnamate | 5.00 | 7.00 | 7.00 | 7.00 | 7.00 | 7.00 | 7.00 | 7.00 | 7.00 |
| | Octocrylene | 10.00 | 8.00 | 8.00 | 8.00 | 8.00 | 8.00 | 8.00 | 8.00 | 8.00 |
| | Methanone, 1,1'-(1,4-piperazinediyl)bis[1-[2-[4-(diethylamino)-2-hydroxybenzoyl]phenyl]- CAS number (919803-06-8) | 1.00 | 2.00 | 2.00 | 2.00 | 2.00 | 2.00 | 2.00 | 2.00 | 2.00 |
| | Diethylamino Hydroxy Benzoyl Hexyl Benzoate | | 4.00 | | | | | | | |
| | Isoamyl p-Methoxycinnamate | | | 2.00 | | | | | | |
| | Ethylhexyl Salicylate | | | | | | | | 5.00 | |
| | 4-Methylbenzylidene Camphor | | | | 2.00 | | | | | |
| Part C | Polyglyceryl-2 Triisostearate | 14.00 | 14.00 | 14.00 | 14.00 | 14.00 | 14.00 | 14.00 | 14.00 | 14.00 |
| | Trimethylolpropane Triisostearate | 10.00 | 10.00 | 10.00 | 10.00 | 10.00 | 10.00 | 10.00 | 10.00 | 10.00 |
| Part D | *Ricinus Communis* (Castor) Seed Oil | Qs. 100 | Qs. 100 | Qs. 100 | Qs. 100 | Qs. 100 | Qs. 100 | Qs. 100 | Qs. 100 | Qs. 100 |
| | CI 17200/Red 33 Lake | 0.27 | 0.27 | 0.27 | 0.27 | 0.27 | 0.27 | 0.27 | 0.27 | 0.27 |
| | CI 15850/Red 7 Lake | 0.07 | 0.07 | 0.07 | 0.07 | 0.07 | 0.07 | 0.07 | 0.07 | 0.07 |
| | CI 77891/Titanium Dioxide (and) Cetyl Dimethicone (WHITE) | 0.67 | 0.67 | 0.67 | 0.67 | 0.67 | 0.67 | 0.67 | 0.67 | 0.67 |
| | Methylene Bis-Benzotriazolyl Tetramethylbutylphenol * | | | | | 3.00 | | | | |
| | Titanium Dioxide *** | | | | | | 2.00 | | | |
| | Tris-Biphenyl Triazine * | | | | | | | 2.00 | | |
| | Zinc Oxide | | | | | | | | | 2.00 |
| Part E | Jojoba Esters | 12.00 | 12.00 | 12.00 | 12.00 | 12.00 | 12.00 | 12.00 | 12.00 | 12.00 |
| Part F | Calcium Sodium Borosilicate (and) Titanium Dioxide (and) Cetyl Dimethicone (and) Tin Oxide/CI 77861 (SILVER) | 2.00 | 2.00 | 2.00 | 2.00 | 2.00 | 2.00 | 2.00 | 2.00 | 2.00 |
| | Calcium Sodium Borosilicate (and) Titanium Dioxide (and) Cetyl Dimethicone (and) Tin Oxide/CI 77861 (GREEN) | 5.00 | 5.00 | 5.00 | 5.00 | 5.00 | 5.00 | 5.00 | 5.00 | 5.00 |

Manufacturing instructions:
Heat phase B to 80° C. during 10 minutes. Grind part D with a 3 roll-mill. In an appropriate vessel, weight part A. Add then part B, C and D. Heat the mix between 98-102° C. under very slow agitation to avoid air bubbles. When everything is melted, add part E and F under slow agitation. When homogeneous, pour into lipstick molds (add previously phenyl trimethicone and heat them at 39-42° C.). When cold, take off the sticks with an appropriate packaging.

| | | |
|---|---|---|
| In vitro SPF measured according the method described | | 18.30 |
| UVA PF measured according the method described | | 5.20 |

| Aqueous Gel FORMULATION | | | | | | | | | |
|---|---|---|---|---|---|---|---|---|---|
| Clear Gel INCI-Name | A % w/w | B % w/w | C % w/w | D % w/w | E % w/w | F % w/w | G % w/w | H % w/w | I % w/w |
| SD Alcohol 40 | 44.07 | 44.07 | 44.07 | 44.07 | 44.07 | 44.07 | 44.07 | 44.07 | 44.07 |
| Hydroxypropyl Cellulose | 1.67 | 1.67 | 1.67 | 1.67 | 1.67 | 1.67 | 1.67 | 1.67 | 1.67 |
| Ethylhexyl Triazone | 5.00 | 5.00 | 5.00 | 5.00 | 5.00 | 5.00 | 5.00 | 5.00 | 5.00 |
| Methanone, 1,1'-(1,4-piperazinediyl)-is[1-[2-[4-(diethylamino)-2-hydroxy-enzoyl]phenyl]- CAS number (919803-06-8) | 5.00 | 5.00 | 5.00 | 5.00 | 5.00 | 5.00 | 5.00 | 5.00 | 5.00 |
| Diethylamino Hydroxy Benzoyl Hexyl Benzoate | | 4.00 | | | | | | | |
| Drometrizole Trisiloxane | | | 2.00 | | | | | | |
| Methylene Bis-Benzotriazolyl Tetra-methylbutylphenol * | | | | | 3.00 | | | | |
| Titanium Dioxide *** | | | | | | 2.00 | | | |
| Tris-Biphenyl Triazine * | | | | | | | 2.00 | | |
| Ethylhexyl Salicylate | | | | | | | | 5.00 | |
| Phenylbenzimidazole Sulfonic Acid | | | | | | | | | 2.00 |
| 4-Methylbenzylidene Camphor | | | | 2.00 | | | | | |
| Isopropyl PPG-2 Isodeceth-7 Carboxylate | 9.64 | 9.64 | 9.64 | 9.64 | 9.64 | 9.64 | 9.64 | 9.64 | 9.64 |
| SD Alcohol 40 | 24.30 | 24.30 | 24.30 | 24.30 | 24.30 | 24.30 | 24.30 | 24.30 | 24.30 |
| Perfume | 0.60 | 0.60 | 0.60 | 0.60 | 0.60 | 0.60 | 0.60 | 0.60 | 0.60 |
| Aqua (Water) | Qsp 100 | Qsp 100 | Qsp 100 | Qsp 100 | Qsp 100 | Qsp 100 | Qsp 100 | Qsp 100 | Qsp 100 |
| Citric Acid (and) Silver Citrate | 0.10 | 0.10 | 0.10 | 0.10 | 0.10 | 0.10 | 0.10 | 0.10 | 0.10 |
| Sclerotium Gum | 0.10 | 0.10 | 0.10 | 0.10 | 0.10 | 0.10 | 0.10 | 0.10 | 0.10 |
| In vitro SPF measured according the method described | | | | | | | | 21.00 | |
| UVA PF measured according the method described | | | | | | | | 6.60 | |

| Oleogel FORMULATION | | | | | | | | | |
|---|---|---|---|---|---|---|---|---|---|
| SUNSCREEN Oleogel INCI-Name | A % w/w | B % w/w | C % w/w | D % w/w | E % w/w | F % w/w | G % w/w | H % w/w | I % w/w |
| Mineral Oil | Qs to 100 | Qs to 100 | Qs to 100 | Qs to 100 | Qs to 100 | Qs to 100 | Qs to 100 | Qs to 100 | Qs to 100 |
| Phenethyl Benzoate | 2.00 | 2.00 | 2.00 | 2.00 | 2.00 | 2.00 | 2.00 | 2.00 | 2.00 |
| Triisodecyl Trimellitate | 1.00 | 1.00 | 1.00 | 1.00 | 1.00 | 1.00 | 1.00 | 1.00 | 1.00 |
| Isopropyl Lauroyl Sarcosinate | 0.50 | 0.50 | 0.50 | 0.50 | 0.50 | 0.50 | 0.50 | 0.50 | 0.50 |
| Polyethylene | 9.75 | 9.75 | 9.75 | 9.75 | 9.75 | 9.75 | 9.75 | 9.75 | 9.75 |
| C12-15 Alkyl Benzoate | 10.00 | 10.00 | 10.00 | 10.00 | 10.00 | 10.00 | 10.00 | 10.00 | 10.00 |
| Isopropyl Palmitate | 9.00 | 9.00 | 9.00 | 9.00 | 9.00 | 9.00 | 9.00 | 9.00 | 9.00 |
| Petrolatum | 5.25 | 5.25 | 5.25 | 5.25 | 5.25 | 5.25 | 5.25 | 5.25 | 5.25 |
| *Aleurites Moluccana* Seed Oil | 4.00 | 4.00 | 4.00 | 4.00 | 4.00 | 4.00 | 4.00 | 4.00 | 4.00 |
| Cetearyl Alcohol (and) Ceteareth-20 | 3.00 | 3.00 | 3.00 | 3.00 | 3.00 | 3.00 | 3.00 | 3.00 | 3.00 |
| *Macadamia Ternifolia* Seed Oil | 2.00 | 2.00 | 2.00 | 2.00 | 2.00 | 2.00 | 2.00 | 2.00 | 2.00 |
| *Arachis Hypogaea* (Peanut) Oil | 1.00 | 1.00 | 1.00 | 1.00 | 1.00 | 1.00 | 1.00 | 1.00 | 1.00 |
| Dimethicone | 0.95 | 0.95 | 0.95 | 0.95 | 0.95 | 0.95 | 0.95 | 0.95 | 0.95 |
| Diethylhexyl Butamido Triazone | 3.00 | 1.00 | 1.00 | 1.00 | 1.00 | 1.00 | 1.00 | 1.00 | 1.00 |
| Methanone, 1,1'-(1,4-piperazinediyl)-is[1-[2-[4-(diethylamino)-2-hydroxy-benzoyl]phenyl]- CAS number (919803-06-8) | 2.00 | 2.00 | 2.00 | 2.00 | 2.00 | 2.00 | 2.00 | 2.00 | 2.00 |
| Diethylamino Hydroxy Benzoyl Hexyl Benzoate | | 4.00 | | | | | | | |
| Zinc Oxide | | | 4.00 | | | | | | |
| Methylene Bis-Benzotriazolyl Tetra-methylbutylphenol * | | | | | 3.00 | | | | |
| Titanium Dioxide *** | | | | | | 2.00 | | | |
| Tris-Biphenyl Triazine * | | | | | | | 2.00 | | |
| Ethylhexyl Salicylate | | | | | | | | 5.00 | |
| Phenylbenzimidazole Sulfonic Acid | | | | | | | | | 2.00 |
| Homosalate | | | | 10.00 | | | | | |
| BHT | 0.05 | 0.05 | 0.05 | 0.05 | 0.05 | 0.05 | 0.05 | 0.05 | 0.05 |
| Perfume | q.s. | q.s. | q.s. | q.s. | q.s. | q.s. | q.s. | q.s. | q.s. |
| In vitro SPF measured according the method described | 23.50 | | | | | | | | |
| UVA PF measured according the method described | 3.80 | | | | | | | | |

| Silicone Gel FORMULATION | | | | | | | | | |
|---|---|---|---|---|---|---|---|---|---|
| Silicone gel formulation<br>INCI-Name | A<br>% w/w | B<br>% w/w | C<br>% w/w | D<br>% w/w | E<br>% w/w | F<br>% w/w | G<br>% w/w | H<br>% w/w | I<br>% w/w |
| Ethylhexyl Methoxycinnamate | 6.00 | 6.00 | 6.00 | 6.00 | 6.00 | 6.00 | 6.00 | 6.00 | 6.00 |
| Octocrylene | 6.00 | 6.00 | 6.00 | 6.00 | 6.00 | 6.00 | 6.00 | 6.00 | 6.00 |
| Methanone, 1,1'-(1,4-piperazinediyl)-is1-[2-[4-(diethylamino)-2-hydroxy-enzoyl]phenyl]- CAS number (919803-06-8) | 4.00 | 4.00 | 4.00 | 4.00 | 4.00 | 4.00 | 4.00 | 4.00 | 4.00 |
| Diethylamino Hydroxy Benzoyl Hexyl Benzoate | | 4.00 | | | | | | | |
| Zinc Oxide | | | 4.00 | | | | | | |
| Methylene Bis-Benzotriazolyl Tetra-methylbutylphenol * | | | | | 3.00 | | | | |
| Titanium Dioxide *** | | | | | | | 2.00 | | |
| Tris-Biphenyl Triazine * | | | | | | | 2.00 | | |
| Ethylhexyl Salicylate | | | | | | | | 5.00 | |
| Phenylbenzimidazole Sulfonic Acid | | | | | | | | | 2.00 |
| Merocyanine of formula (A) or (B) | | | | 0.50 | | 4.00 | | | |
| Isopropyl Isostearate | 0.00 | 0.00 | 0.00 | 0.00 | 0.00 | 4.00 | 0.00 | 0.00 | 0.00 |
| Isopropyl Lauroyl Sarcosinate | 7.50 | 7.50 | 7.50 | 15.00 | 7.50 | 4.00 | 10.00 | 0.00 | 0.00 |
| Phenethyl Benzoate | 0.00 | 0.00 | 0.00 | 0.00 | 0.00 | 4.00 | 0.00 | 0.00 | 10.00 |
| Tocopheryl Acetate | 0.10 | 0.00 | 0.10 | 2.00 | 0.00 | 0.00 | 0.10 | 0.00 | 0.00 |
| Cyclopentasiloxane (and) Dimethicone Crosspolymer | Qs 100 | Qs 100 | Qs 100 | Qs 100 | Qs 100 | Qs 100 | Qs 100 | Qs 100 | Qs 100 |
| Cyclopentasiloxane (and) Dimethicone/Vinyl Dimethicone Crosspolymer | 0.00 | 0.00 | 0.00 | 0.00 | 0.00 | 0.00 | 0.00 | 0.00 | 50.00 |
| Phenyl Trimethicone (and) Dimethicone/Phenyl Vinyl Dimethicone Crosspolymer | 0.00 | 0.00 | 0.00 | 0.00 | 0.00 | 0.00 | 0.00 | 0.00 | 10.00 |
| Dimethicone (and) Dimethicone/-Polyglycerin-3 Crosspolymer | 0.00 | 0.00 | 0.00 | 0.00 | 0.00 | 0.00 | 0.00 | 0.00 | 10.00 |
| PEG-15/Lauryl Dimethicone Crosspolymer (and) Mineral Oil | 20.00 | 17.80 | 20.00 | 15.00 | 31.00 | 20.00 | 20.00 | 15.00 | 0.00 |
| Cyclomethicone D5 | 0.00 | 12.00 | 0.00 | 0.00 | 0.00 | 0.00 | 0.00 | 30.00 | 0.00 |
| Polymethylsilsesquioxane | 10.00 | 0.00 | 0.00 | 0.00 | 12.00 | 4.90 | 0.00 | 2.00 | 0.00 |
| Boron Nitride | 0.00 | 7.00 | 0.00 | 10.00 | 0.00 | 7.00 | 0.00 | 0.00 | 10.00 |
| Nylon-12 | 0.00 | 0.00 | 10.00 | 0.00 | 5.00 | 0.00 | 10.00 | 5.00 | 0.00 |
| PTFE | 0.00 | 0.00 | 0.00 | 0.00 | 3.00 | 3.00 | 0.00 | 0.00 | 0.00 |
| Iron Oxides (RED) | 0.00 | 0.00 | 0.10 | 0.10 | 0.00 | 0.10 | 0.00 | 0.00 | 0.00 |
| Mica and Iron Oxides | 0.00 | 0.10 | 0.00 | 0.00 | 0.00 | 0.00 | 0.00 | 0.00 | 0.00 |
| Perfume | 0.20 | 0.20 | 0.20 | 0.20 | 0.00 | 0.00 | 0.00 | 0.00 | 0.00 |
| Aqua (Water) | 0.00 | 0.00 | 0.00 | 0.00 | 0.00 | 0.00 | 0.80 | 0.00 | 0.00 |
| In vitro SPF measured according the method described | 20.40 | | | | | | | | |
| UVA PF measured according the method described | 8.30 | | | | | | | | |

| Make-up FORMULATION | | | | | | | | | | |
|---|---|---|---|---|---|---|---|---|---|---|
| | W/Si Natural Foundation Veil<br>INCI-Name | A<br>% w/w | B<br>% w/w | C<br>% w/w | D<br>% w/w | E<br>% w/w | F<br>% w/w | G<br>% w/w | H<br>% w/w | I<br>% w/w |
| Part A | Cetyl PEG/PPG-10/1 Dimethicone | 4.70 | 4.70 | 4.70 | 4.70 | 4.70 | 4.70 | 4.70 | 4.70 | 4.70 |
| | Polyglyceryl-4 Isostearate (and) Cetyl PEG/PPG-10/1 Dimethicone (and) Hexyl Laurate | 3.50 | 3.50 | 3.50 | 3.50 | 3.50 | 3.50 | 3.50 | 3.50 | 3.50 |
| | Isopropyl Myristate (and) Steralkoium Hectorite (and) Propylene Carbonate | 5.25 | 5.25 | 5.25 | 5.25 | 5.25 | 5.25 | 5.25 | 5.25 | 5.25 |
| | Cyclopentasiloxane | 14.00 | 14.00 | 14.00 | 14.00 | 14.00 | 14.00 | 14.00 | 14.00 | 14.00 |
| | Cyclopentasiloxane (and) Cycloexasiloxane | 8.50 | 8.50 | 8.50 | 8.50 | 8.50 | 8.50 | 8.50 | 8.50 | 8.50 |
| | Isododecane | 5.80 | 5.80 | 5.80 | 5.80 | 5.80 | 5.80 | 5.80 | 5.80 | 5.80 |
| | Isoeicosane | 3.00 | 3.00 | 3.00 | 3.00 | 3.00 | 3.00 | 3.00 | 3.00 | 3.00 |
| | Ethylhexyl Methoxycinnamate | 10.00 | 10.00 | 10.00 | 10.00 | 10.00 | 10.00 | 10.00 | 10.00 | 10.00 |
| | Bis-Ethylhexyloxyphenol Methoxyphenyl Triazine | 4.00 | 4.00 | 4.00 | 4.00 | 4.00 | 4.00 | 4.00 | 4.00 | 4.00 |
| | Diethylamino Hydroxy Benzoyl Hexyl Benzoate | | 4.00 | | | | | | | |
| | Zinc Oxide | | | 4.00 | | | | | | |
| | Titanium Dioxide *** | | | | | | | 2.00 | | |
| | Ethylhexyl Salicylate | | | | | | | | 5.00 | |
| | Merocyanine of formula (A) or (B) | | | | 1.00 | | | | | |

Make-up FORMULATION

| | W/Si Natural Foundation Veil INCI-Name | A % w/w | B % w/w | C % w/w | D % w/w | E % w/w | F % w/w | G % w/w | H % w/w | I % w/w |
|---|---|---|---|---|---|---|---|---|---|---|
| Part B | CI 77891/Titanium Dioxide (and) Cetyl Dimethicone (WHITE) | 5.00 | 5.00 | 5.00 | 5.00 | 5.00 | 5.00 | 5.00 | 5.00 | 5.00 |
| | CI 77492/Iron Oxides (and) Cetyl Dimethicone (YELLOW) | 0.92 | 0.92 | 0.92 | 0.92 | 0.92 | 0.92 | 0.92 | 0.92 | 0.92 |
| | CI 77491/Iron Oxides (and) Cetyl Dimethicone (RED) | 0.26 | 0.26 | 0.26 | 0.26 | 0.26 | 0.26 | 0.26 | 0.26 | 0.26 |
| | CI 77499/Iron Oxides (and) Cetyl Dimethicone (BLACK) | 0.20 | 0.20 | 0.20 | 0.20 | 0.20 | 0.20 | 0.20 | 0.20 | 0.20 |
| Part C | Aqua (Water) | qs to 100 | qs to 100 | qs to 100 | qs to 100 | qs to 100 | qs to 100 | qs to 100 | qs to 100 | qs to 100 |
| | Phenylbenzimidazole Sulfonic Acid | | | | | | | | | 2.00 |
| | Butylene Glycol | 5.00 | 5.00 | 5.00 | 5.00 | 5.00 | 5.00 | 5.00 | 5.00 | 5.00 |
| | Sodium Chloride | 0.80 | 0.80 | 0.80 | 0.80 | 0.80 | 0.80 | 0.80 | 0.80 | 0.80 |
| | Sodium Stearoyl Glutamate | 0.50 | 0.50 | 0.50 | 0.50 | 0.50 | 0.50 | 0.50 | 0.50 | 0.50 |
| Part D | Methanone, 1,1'-(1,4-piperainediyl)bis[1-[2-[4-(diethylamino)-2-hydroxybenzoyl]phenyl]- CAS number (919803-06-8) | 1.50 | 1.50 | 1.50 | 1.50 | 1.50 | 1.50 | 1.50 | 1.50 | 1.50 |
| | Methylene Bis-Benzotriazolyl Tetramethylbutylphenol * | | | | | 3.00 | | | | |
| | Tris-Biphenyl Triazine * | | | | | | | | 2.00 | |
| Part E | Polymethyl Methacrylate | 4.00 | 4.00 | 4.00 | 4.00 | 4.00 | 4.00 | 4.00 | 4.00 | 4.00 |
| | Preservatives | qs | qs | qs | qs | qs | qs | qs | qs | qs |

Manufacturing Instruction:
Prepare part A: add each ingredient to the main vessel and mix well after each. When part A is homogeneous, add part B (previously milled) to part A. Mix C separately. When the two phases are homogeneous, add part C slowly into part A/B under stirrer (Rayneri type). Add part D under stirring, and finally the ingredients of part E.

| | |
|---|---|
| In vitro SPF measured according the method described | 33.10 |
| UVA PF measured according the method described | 12.20 |

| | Water resistant Mascara INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Aqua (Water) | Qs. 100 | Qs. 100 | Qs. 100 | Qs. 100 | Qs. 100 | Qs. 100 | Qs. 100 | Qs. 100 | Qs. 100 |
| | Xanthan Gum | 0.20 | 0.20 | 0.20 | 0.20 | 0.20 | 0.20 | 0.20 | 0.20 | 0.20 |
| | Methylparaben | 0.25 | 0.25 | 0.25 | 0.25 | 0.25 | 0.25 | 0.25 | 0.25 | 0.25 |
| | PVP | 2.50 | 2.50 | 2.50 | 2.50 | 2.50 | 2.50 | 2.50 | 2.50 | 2.50 |
| | Mica (and) Silica | 2.00 | 2.00 | 2.00 | 2.00 | 2.00 | 2.00 | 2.00 | 2.00 | 2.00 |
| | Iron Oxides (Black Iron Oxide C7133) | 7.00 | 7.00 | 7.00 | 7.00 | 7.00 | 7.00 | 7.00 | 7.00 | 7.00 |
| | Ultramarines (Ultramarine Blue 7104) | 0.10 | 0.10 | 0.10 | 0.10 | 0.10 | 0.10 | 0.10 | 0.10 | 0.10 |
| | Triethanolamine, 99% | 1.00 | 1.00 | 1.00 | 1.00 | 1.00 | 1.00 | 1.00 | 1.00 | 1.00 |
| Part B | *Copernicia Cerifera* (Carnauba) Wax | 8.00 | 8.00 | 8.00 | 8.00 | 8.00 | 8.00 | 8.00 | 8.00 | 8.00 |
| | Beeswax, white | 4.00 | 4.00 | 4.00 | 4.00 | 4.00 | 4.00 | 4.00 | 4.00 | 4.00 |
| | Polyisobutene | 6.00 | 6.00 | 6.00 | 6.00 | 6.00 | 6.00 | 6.00 | 6.00 | 6.00 |
| | Stearic Acid | 2.50 | 2.50 | 2.50 | 2.50 | 2.50 | 2.50 | 2.50 | 2.50 | 2.50 |
| | Glyceryl Stearate | 1.00 | 1.00 | 1.00 | 1.00 | 1.00 | 1.00 | 1.00 | 1.00 | 1.00 |
| | Propylparaben | 0.20 | 0.20 | 0.20 | 0.20 | 0.20 | 0.20 | 0.20 | 0.20 | 0.20 |
| | Butyl Methoxydibenzoylmethane | 2.00 | 2.00 | 2.00 | 2.00 | 2.00 | 2.00 | 2.00 | 2.00 | 2.00 |
| | Diethylamino Hydroxy Benzoyl Hexyl Benzoate | | 4.00 | | | | | | | |
| | Ethylhexyl Salicylate | | | | | | | | 5.00 | |
| | Malonate of Formula (C) or (D) | | | | 10.00 | | | | | |
| Part C | Methanone, 1,1'-(1,4-piperazinediyl)bis[1-[2-[4-(diethylamino)-2-hydroxybenzoyl]phenyl]- CAS number (919803-06-8) | 3.00 | 3.00 | 3.00 | 3.00 | 3.00 | 3.00 | 3.00 | 3.00 | 3.00 |
| | Methylene Bis-Benzotriazolyl Tetramethylbutylphenol * | | | | | 3.00 | | | | |
| | Titanium Dioxide *** | | | | | | 2.00 | | | |
| | Tris-Biphenyl Triazine * | | | | | | | 2.00 | | |
| | Phenylbenzimidazole Sulfonic Acid | | | | | | | | | 2.00 |
| | Bis-Ethylhexyloxyphenol Methoxyphenyl Triazine ** | | | 2.00 | | | | | | |
| | Aqua (Water) | 1.00 | 1.00 | 1.00 | 1.00 | 1.00 | 1.00 | 1.00 | 1.00 | 1.00 |
| | Imidazolidinyl Urea | 0.10 | 0.10 | 0.10 | 0.10 | 0.10 | 0.10 | 0.10 | 0.10 | 0.10 |
| | Acrylates/Ammonium Methacrylate Copolymer | 12.00 | 12.00 | 12.00 | 12.00 | 12.00 | 12.00 | 12.00 | 12.00 | 12.00 |

| Water resistant Mascara INCI-Name | A % w/w | B % w/w | C % w/w | D % w/w | E % w/w | F % w/w | G % w/w | H % w/w | I % w/w |
|---|---|---|---|---|---|---|---|---|---|

Manufacturing Instruction:
Slowly add xanthan gum into a vortex of water, using low-shear agitation, dispersed completely. Heat to 60-70° C. Premix the powder in a blender to pulverize the öaterials, and until the pigments are uniformly dispersed. Add the premixed A, mixing constantly and slowly adding the rest of the ingredients. Mix 10 min, then homogeneize for 5 mon. Combine B and heta to 80° C. Homogeneize A and add B to A under moderate agitation. Let cool down to 40° C. and add premixed C. Let cool down to RT under agitation.

| | | | | | | | | | |
|---|---|---|---|---|---|---|---|---|---|
| In vitro SPF measured according the method described | | | | | | | | 3.50 | |
| UVA PF measured according the method described | | | | | | | | 7.50 | |

Cationic FORMULATION

| | Cationic O/W sun cream INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Palmitamidopropyltrimonium Chloride | 6.00 | 6.00 | 6.00 | 6.00 | 6.00 | 6.00 | 6.00 | 6.00 | 6.00 |
| | Stearyl Alcohol | 2.00 | 2.00 | 2.00 | 2.00 | 2.00 | 2.00 | 2.00 | 2.00 | 2.00 |
| | Isocetyl Palmitate | 4.00 | 4.00 | 4.00 | 4.00 | 4.00 | 4.00 | 4.00 | 4.00 | 4.00 |
| | Decyl Cocoate | 3.00 | 3.00 | 3.00 | 3.00 | 3.00 | 3.00 | 3.00 | 3.00 | 3.00 |
| | C12-15 Alkyl Benzoate | 3.00 | 3.00 | 3.00 | 3.00 | 3.00 | 3.00 | 3.00 | 3.00 | 3.00 |
| | Cetyl Dimethicone | 0.75 | 0.75 | 0.75 | 0.75 | 0.75 | 0.75 | 0.75 | 0.75 | 0.75 |
| | Ethylhexyl Triazone | 4.00 | 2.00 | 2.00 | 2.00 | 2.00 | 2.00 | 2.00 | 2.00 | 2.00 |
| | Diethylamino Hydroxy Benzoyl Hexyl Benzoate | | 4.00 | | | | | | | |
| | Ethylhexyl Salicylate | | | | | | | | 5.00 | |
| | Malonate of Formula (C) or (D) | | | | 5.00 | | | | | |
| Part B | Methanone, 1,1'-(1,4-piperazinediyl)-is[1-[2-[4-(diethylamino)-2-hydroxy-enzoyl]phenyl]- CAS number (919803-06-8) | 4.00 | 2.00 | 2.00 | 2.00 | 2.00 | 2.00 | 2.00 | 2.00 | 2.00 |
| | Bis-Ethylhexyloxyphenol Methoxyhenyl Triazine ** | | | 2.00 | | | | | | |
| | Methylene Bis-Benzotriazolyl Tetra-ethylutylphenol * | | | | | | 3.00 | | | |
| | Titanium Dioxide *** | | | | | | | 2.00 | | |
| | Tris-Biphenyl Triazine * | | | | | | | | 2.00 | |
| | Phenylbenzimidazole Sulfonic Acid | | | | | | | | | 2.00 |
| | Aqua (Water) | Qs to 100 | Qs to 100 | Qs to 100 | Qs to 100 | Qs to 100 | Qs to 100 | Qs to 100 | Qs to 100 | Qs to 100 |
| | Glycerin | 3.00 | 3.00 | 3.00 | 3.00 | 3.00 | 3.00 | 3.00 | 3.00 | 3.00 |
| | Trisodium EDTA | 0.10 | 0.10 | 0.10 | 0.10 | 0.10 | 0.10 | 0.10 | 0.10 | 0.10 |
| Part C | Capryl/Capramidopropyl Betaine | 8.00 | 8.00 | 8.00 | 8.00 | 8.00 | 8.00 | 8.00 | 8.00 | 8.00 |
| | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.80 | 0.80 | 0.80 | 0.80 | 0.80 | 0.80 | 0.80 | 0.80 | 0.80 |
| | In vitro SPF measured according the method described | | | | | | | | 15.70 | |
| | UVA PF measured according the method described | | | | | | | | 5.50 | |

Si/W FORMULATION

| | Si/W sun cream INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Cyclopentasiloxane (and) Dimethicone/Vinyl Dimethicone Crosspolymer | 8.00 | 8.00 | 8.00 | 8.00 | 8.00 | 8.00 | 8.00 | 8.00 | |
| | Dimethicone (and) Dimethione/Vinyl Dimethicone Crosspolymer | 30.00 | 30.00 | 30.00 | 30.00 | 30.00 | 30.00 | 30.00 | 30.00 | 30.00 |
| | Cyclopentasiloxane | 10.00 | 10.00 | 10.00 | 10.00 | 10.00 | 10.00 | 10.00 | 10.00 | 10.00 |
| | Diethylhexyl Butamido Triazone | 3.00 | 1.00 | 1.00 | 1.00 | 1.00 | 1.00 | 1.00 | 1.00 | 1.00 |
| | Diethylamino Hydroxy Benzoyl Hexyl Benzoate | | 4.00 | | | | | | | |
| | Ethylhexyl Salicylate | | | | | | | | 5.00 | |
| | Malonate of Formula (C) or (D) | | | | 5.00 | | | | | |
| | Bis-Ethylhexyloxyphenol Methoxyphenyl Triazine | | | 2.00 | | | | | | |

-continued

| | Si/W sun cream<br>INCI-Name | A<br>% w/w | B<br>% w/w | C<br>% w/w | D<br>% w/w | E<br>% w/w | F<br>% w/w | G<br>% w/w | H<br>% w/w | I<br>% w/w |
|---|---|---|---|---|---|---|---|---|---|---|
| Part B | Methanone, 1,1'-(1,4-piperazineiyl)-is[1-[2-[4-(diethylamino)-2-hydroybenzoyl]phenyl]- CAS number (919803-06-8) | 4.00 | 2.00 | 2.00 | 2.00 | 2.00 | 2.00 | 2.00 | 2.00 | 2.00 |
| | Methylene Bis-Benzotriazolyl Tetramethylbutylphenol * | | | | | 3.00 | | | | |
| | Titanium Dioxide *** | | | | | | | 2.00 | | |
| | Tris-Biphenyl Triazine * | | | | | | | | 2.00 | |
| | Phenylbenzimidazole Sulfonic Acid | | | | | | | | | 2.00 |
| | Bis-Ethylhexyloxyphenol Methoxyphenyl Triazine ** | | | 2.00 | | | | | | |
| | Butylene Glycol | 3.00 | 3.00 | 3.00 | 3.00 | 3.00 | 3.00 | 3.00 | 3.00 | 3.00 |
| | Polyglyceryl-3 Disiloxane Dimethicone | 0.60 | 0.60 | 0.60 | 0.60 | 0.60 | 0.60 | 0.60 | 0.60 | 0.60 |
| | Polyglyceryl-3 Polydimethylsiloxyethyl Dimethicone | 0.30 | 0.30 | 0.30 | 0.30 | 0.30 | 0.30 | 0.30 | 0.30 | 0.30 |
| | Acrylamide/Sodium Acryloyldimethyltaurate Copolymer (and) Isohexadecane (and) Polysorbate 80 | 0.60 | 0.60 | 0.60 | 0.60 | 0.60 | 0.60 | 0.60 | 0.60 | 0.60 |
| | Ammonium Acryloyldimethyltaurate/VP Copolymer | 0.65 | 0.65 | 0.65 | 0.65 | 0.65 | 0.65 | 0.65 | 0.65 | 0.65 |
| | Sodium Chloride | 0.10 | 0.10 | 0.10 | 0.10 | 0.10 | 0.10 | 0.10 | 0.10 | 0.10 |
| | Aqua (Water) | Qs to 100 | Qs to 100 | Qs to 100 | Qs to 100 | Qs to 100 | Qs to 100 | Qs to 100 | Qs to 100 | Qs to 100 |
| | In vitro SPF measured according the method described | 12.80 | | | | | | | | |
| | UVA PF measured according the method described | 5.50 | | | | | | | | |

Legend:
* particulate organic filter 50-200 nm, aqueous dispersion, active ingredient w/w %
** particulate organic filter 50-200 nm, encapsulated active ingredient w/w %
*** particulate inorganic filter 10-200 nm, active ingredient w/w %

Methods:

Method to Assess in vitro Sun Protection Factor Measurement (SPF)

End-product application rate 1.4 mg/cm² on PMMA plates (Helioplates®)

UV Transmittance analysis with Labsphere UV-1000S Transmittance Analyser $$SPF = \frac{\int_{290\,nm}^{400\,nm} E_\lambda \cdot S_\lambda \cdot d\lambda}{\int_{290\,nm}^{400\,nm} E_\lambda \cdot S_\lambda \cdot T_\lambda \cdot d\lambda}$$

wherein El=erythema action spectrum; Sl=solar spectral irradiance and Tl=spectral transmittance of the sample.

Method to Assess in vitro UVA Protection Factor (UVA PF)

End-product application rate 1.2 mg/cm² on PMMA plates (Helioplates®)

UV Transmittance analysis with Labsphere UV-1000S Transmittance Analyser

Pre-irradiation step (to take the sun care product photostability into account) via a solar simulator such as Atlas Suntest CPS+

$$PFUVA = \frac{\sum_{320}^{400} \Delta\lambda}{\sum_{320}^{400} T_\lambda \cdot \Delta\lambda} = \frac{1}{T_m}$$

Wherein Tl=sunscreen product transmittance at wave length l and Tm=mean arithmetical value of Transmittance data in the UVA range.

The cosmetic preparation according to the invention is distinguished by excellent protection of human skin against the damaging effect of sunlight.

The following example illustrates the invention.

EXAMPLE 1

Photodegradation of UV Absorber Combinations

For the determination of photodegradation the so-called "plate-test" is employed:

2 μl/cm² of the formulations are spread on quartz plates (sand-blasted surface of 2.8 cm²), and rinsed off the plates after 0, 5, 10, 20, and 50 MED of UV irradiation using an Atlas CPS+ solar simulator.

| Tested formulation comprising components (a), (b) and (c): | |
|---|---|
| Component (a) | Piperazine bi-aminobenzophenone |
| Component (b) | Ethylhexyl Methoxycinnamate |
| Component (c) | Octocrylene |

| Tested formulation comprising components (a), (b) and (c): | |
|---|---|
| Component (d) | Bis-ethylhexyloxyphenol methoxyphenyl triazine |
| Component (e) | Ethylhexl triazone |
| Component (f) | Di-octyl butamido triazone |

Results

The results of combinations with components (a), (b), and (c) are listed in Table 3.

The substances tagged with an asterix (*) are those the recovery percentages refer to. The percentage of component (a) refers to the active.

The experimental error in terms of the standard deviation is in the range of ±3%.

TABLE 3

Recovery of component (b) after irradiation in presence of components (a) and (c)

| Formulation | Component (a) | Component (b) | Component (c) | 0 MED | 5 MED | 10 MED | 20 MED | 50 MED |
|---|---|---|---|---|---|---|---|---|
| 1 | 2% | 2%* | — | 100.0 | 69.4 | 49.7 | 35.7 | 19.1 |
| 2 | 2% | 2%* | 2% | 100.0 | 77.1 | 68.3 | 58.7 | 35.5 |
| 3 | 2% | 2%* | 5% | 100.0 | 83.7 | 77.0 | 72.0 | 50.8 |
| 4 | 2% | 2%* | 10% | 100.0 | 88.5 | 81.8 | 79.7 | 57.4 |

The results of Table 3 show that in the combination of ethylhexyl methoxycinnamate and piperazine bi-aminobenzophenone the ethylhexyl methoxycinnamate can be stabilized by addition of octocrylene.

The results of combinations with components (a), (b), and (d) are listed in Table 4.

The substances tagged with an asterix (*) are those the recovery percentages refer to. The percentage of component (a) refers to the active.

The experimental error in terms of the standard deviation is in the range of ±3%.

TABLE 4

Recovery of component (b) after irradiation in presence of components (a) and (d)

| Formulation | Component (a) | Component (b) | Component (d) | 0 MED | 5 MED | 10 MED | 20 MED | 50 MED |
|---|---|---|---|---|---|---|---|---|
| 1 | 2% | 2%* | — | 100.0 | 69.4 | 49.7 | 35.7 | 19.1 |
| 2 | 2% | 2%* | 1.5% | 100.0 | 79.5 | 67.8 | 64.5 | 42.2 |
| 3 | 2% | 2%* | 2% | 100.0 | 83.3 | 71.0 | 66.9 | 45.2 |
| 4 | 2% | 2%* | 3% | 100.0 | 85.1 | 76.2 | 69.6 | 41.9 |

The results of Table 4 show that in the combination of ethylhexyl methoxycinnamate and piperazine bi-aminobenzophenone the ethylhexyl methoxycinnamate can be stabilized by addition of bis-ethylhexyloxyphenol methoxyphenyl triazine.

The results of combinations with components (a), (b), and (d) are listed in Table 5.

The substances tagged with an asterix (*) are those the recovery percentages refer to. The percentage of component (a) refers to the active.

The experimental error in terms of the standard deviation is in the range of ±3%.

TABLE 5

Recovery of components (e) and (f) after irradiation in presence of component (a)

| Formulation | Component (a) | Component (e) | Component (f) | 0 MED | 5 MED | 10 MED | 20 MED | 50 MED |
|---|---|---|---|---|---|---|---|---|
| 1 | — | 2* | — | 100.0 | 94.4 | 89.4 | 76.5 | 48.9 |
| 2 | 2% | 2%* | — | 100.0 | 97.6 | 96.4 | 93.5 | 79.5 |
| 3 | — | — | 2%* | 100.0 | 88.5 | 82.6 | 70.3 | 37.4 |
| 4 | 2% | — | 2%* | 100.0 | 88.9 | 84.7 | 75.7 | 55.0 |

The results of Table 5 show that both, ethylhexyl triazone and di-octyl butamido triazone are photostabilized in the presence of piperazine bi-aminobenzophenone.

The invention claimed is:

1. A method of treating the combination of components $(b_1)$ and $(c_1)$ in a cosmetic composition in need of stabilization comprising
   the step of adding 2 to 10% by weight of UV absorber
   ($a_1$) 2-ethylhexyl 2-cyano-3,3-diphenylacrylate to the cosmetic composition, which comprises 0.1 to 2% by weight of organic UV absorber

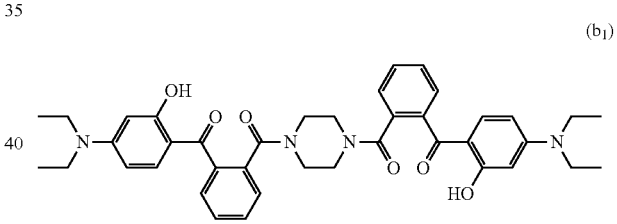

(b₁)

and
   0.1 to 2 % by weight of UV filter ($c_1$) 2-ethylhexyl 4-methoxycinnamate,
   wherein the combination ($b_1$) and ($c_1$) is more stable to light when ($a_1$) is added to the combination.

2. The method according to claim 1, wherein the organic UV absorber ($b_1$), is used in micronized form.